United States Patent
Zhang et al.

(10) Patent No.: US 7,235,712 B1
(45) Date of Patent: Jun. 26, 2007

(54) **BACTERIAL ISOLATES OF THE GENUS *KLEBIELLA*, AND AN ISOMALTULOSE SYNTHASE GENE ISOLATED THEREFROM**

(75) Inventors: Lian Hui Zhang, Singapore (SG); Xianzhen Li, Singapore (SG); Daohai Zhang, Singapore (SG)

(73) Assignee: Agency for Science, Technology and Research, Singapore (SG)

( * ) Notice: Subject to any disclaimer, the term of this patent is extended or adjusted under 35 U.S.C. 154(b) by 0 days.

(21) Appl. No.: 10/203,963

(22) PCT Filed: Feb. 15, 2000

(86) PCT No.: PCT/SG00/00023

§ 371 (c)(1),
(2), (4) Date: Feb. 20, 2003

(87) PCT Pub. No.: WO01/60993

PCT Pub. Date: Aug. 23, 2001

(51) Int. Cl.
*C12N 15/31* (2006.01)
*C12N 15/82* (2006.01)
*C12N 15/61* (2006.01)
*C12N 15/62* (2006.01)
*A01H 5/00* (2006.01)

(52) U.S. Cl. ............ 800/288; 800/278; 800/284; 800/300.1; 800/308; 536/23.1; 536/23.2; 536/23.7; 536/23.4; 435/69.1; 435/468; 435/320.1; 435/412; 435/69.8

(58) Field of Classification Search ............... None
See application file for complete search history.

(56) References Cited

U.S. PATENT DOCUMENTS 5,786,140 A * 7/1998 Mattes et al. ............... 435/6
5,866,791 A * 2/1999 Holt .......................... 800/298
5,985,668 A 11/1999 Klein et al.

FOREIGN PATENT DOCUMENTS

WO WO 95/20047 7/1995

OTHER PUBLICATIONS

Zhang et al 2002 Applied and Environmental Microbiology 68:2676-2682 p. 2676.*
Stephanopoulos et al 1993 Trends in Biotechnology 11:392-396 pp. 393 and 394.*
Tsuyuki, et al., "Isolation and characterization of isomaltulose- and trehalulose-producing bacteria from Thailand soil." *Journal of General and Applied Microbiology*, vol. 38, No. 5, 1992, pp. 483-490.
Huang, et al., "Conversion of sucrose to isomaltulose by *Klebisella planticola* CCRC 191112." *Journal of Industrial Microbiology and Biotechnology*, vol. 21, No. 1-2, Jul. 1998, pp. 22-27.
Park, et al., "Conversion of sucrose to isomaltulose by microbial glucosyltransferase." *Biotechnology Letters*, vol. 14, No. 7, 1992, pp. 547-551.

* cited by examiner

*Primary Examiner*—David T. Fox
*Assistant Examiner*—Brent T Page
(74) *Attorney, Agent, or Firm*—Rothwell, Figg, Ernst & Manbeck P.C.

(57) ABSTRACT

Two strains of a novel bacterial species, *Klebsiella singaporensis* LX3 and LX21, are claimed. A nucleotide sequence (kis) encoding a novel form of isomaltulose synthase, KIS, is also claimed. Also claimed is a method for production of isomaltulose in a plant, which method comprises introducing into a cell of such plant a nucleic acid sequence which encodes an enzyme which converts sucrose into isomaltulose in a manner which allows said cell to express said nucleic acid sequence, as well as a functional cloning method of isolating nucleotide sequence encoding the KIS protein comprising the steps of (a) preparing a gene bank from a donor organism that contains a DNA sequence coding for an isomaltulose biosynthesis activity in a suitable host organism, (b) screening the clones of interest from the gene bank by their enhanced reducing sugar content, and (c) isolating the clones which contain a DNA coding for a protein with isomaltulose biosynthesis activity.

15 Claims, 10 Drawing Sheets

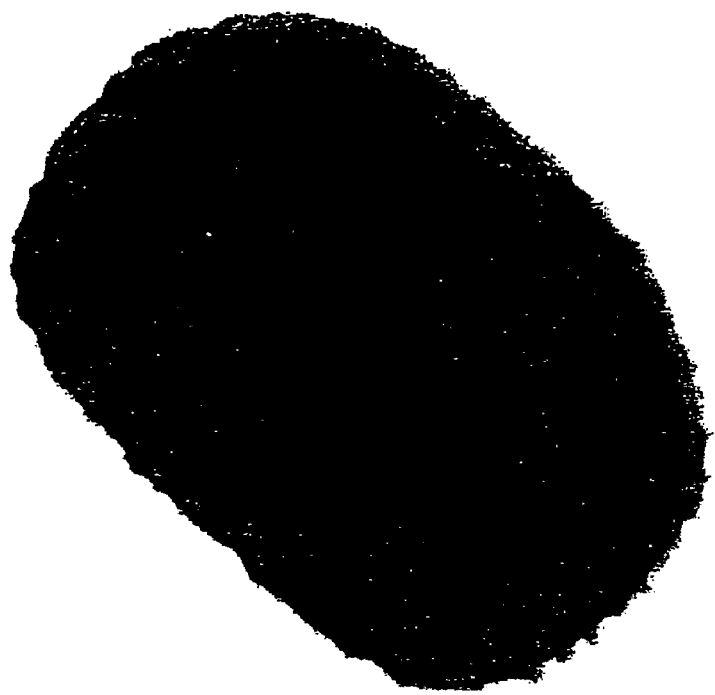
Figure 1.

Figure 6A

| | |
|---|---|
| ......................gatatcactggta | -201 |
| ttatggagtattatactccccccttatttactcatcaaagccaggcgttc | -151 |
| cactctgcctccggtatataactttccgggaaacaatcccttcctgaaaa | -101 |
| taattattgttaccggagtcatactctggctattgatgatttacgc<u>tttt</u> | -51 |
|        -10                         SD | |
| <u>ctttaataacaatt</u>cgtctcattcacaactgactttgca<u>agga</u>aattatt | -1 |
| ATGTCTTTTGTTACGCTACGTACCGGGGTGGCTGTCGCGCTGTCATCTTT | 50 |
| GATAATAAGTCTGGCCTGCCCGGCTGTCAGTGCTGCACCATCCTTGAATC | 100 |
| AGGATATTCACGTTCAAAAGGAAAGTGAATATCCTGCATGGTGGAAAGAA | 150 |
| GCTGTTTTTTATCAGATCTATCCTCGCTCATTTAAAGACACCAATGATGA | 200 |
| TGGCATTGGCGATATTCGCGGTATTATTGAAAAGCTGGACTATCTGAAAT | 250 |
| CGCTCGGTATTGACGCTATCTGGATCAATCCCCATTACGACTCTCCGAAC | 300 |
| ACCGATAACGGCTATGACATCAGTAATTATCGTCAGATAATGAAAGAGTA | 350 |
| TGGCACAATGGAGGATTTTGATAGCCTTGTTGCCGAAATGAAAAAACGAA | 400 |
| ATATGCGCTTAATGATCGACGTGGTCATTAACCATACCAGTGATCAACAC | 450 |
| CCGTGGTTTATTCAGAGTAAAAGCGATAAAAACAACCCTTATCGTGACTA | 500 |
| TTATTTCTGGCGTGACGGAAAAGATAATCAGCCACCTAATAATTACCCCT | 550 |
| CATTTTTCGGCGGCTCGGCATGGCAAAAAGATGCAAAGTCAGGACAGTAC | 600 |
| TATTTACACTATTTTGCCAGACAGCAACCTGATCTCAACTGGGATAACCC | 650 |
| GAAAGTACGTGAGGATCTTTACGCAATGCTCCGCTTCTGGCTGGATAAAG | 700 |
| GCGTTTCAGGCATGCGATTTGATACGGTGGCAACTTATTCCAAAATCCCG | 750 |
| GGATTTCCCAATCTGACACCTGAACAACAGAAAAATTTTGCTGAACAATA | 800 |
| CACCATGGGGCCTAATATTCATCGATACATTCAGGAAATGAACCGGAAAG | 850 |
| TTCTGTCCCGGTATGATGTGGCCACCGCGGGTGAAATTTTGGCGTCCCG | 900 |
| CTGGATCGTTCGTCGCAGTTTTTTGATCGCCGCCGACATGAGCTGAATAT | 950 |

Figure 6B

| | |
|---|---|
| GGCGTTTATGTTTGACCTCATTCGTCTCGATCGCGACAGCAATGAACGCT | 1000 |
| GGCGTCACAAGTCGTGGTCGCTCTCTCAGTTCCGCCAGATCATCAGCAAA | 1050 |
| ATGGATGTCACGGTCGGAAAGTATGGCTGGAACACGTTCTTCTTAGATAA | 1100 |
| CCATGACAACCCCCGTGCGGTATCTCACTTCGGGGATGACAGGCCGCAAT | 1150 |
| GGCGGGAGGCGTCGGCTAAGGCACTGGCGACGATTACCCTCACTCAGCGG | 1200 |
| GCGACGCCGTTTATTTATCAGGGTTCAGAGCTGGGAATGACTAATTATCC | 1250 |
| CTTCAGGCAACTCAACGAATTTGACGACATCGAGGTCAAAGGTTTCTGGC | 1300 |
| AGGATTATGTCCAGAGTGGAAAAGTCACGGCCACAGAGTTTCTCGATAAT | 1350 |
| GTGCGCCTGACGAGCCGCGATAACAGCAGAACACCTTTCCAGTGGAATGA | 1400 |
| CACCCTGAATGCTGGTTTTACTCGCGGAAAGCCGTGGTTTCACATCAACC | 1450 |
| CAAACTATGTGGAGATCAACGCCGAACGCGAAGAAACCCGCGAAGATTCA | 1500 |
| GTGCTGAATTACTATAAAAAAATGATTCAGCTACGCCACCATATCCCTGC | 1550 |
| TCTGGTATATGGCGCCTATCAGGATCTTAATCCACAGGACAATACCGTTT | 1600 |
| ATGCCTATACCCGAACGCTGGGTAACGAGCGTTATCTGGTCGTGGTGAAC | 1650 |
| TTTAAGGAGTACCCGGTCCGCTATACTCTCCCGGCTAATGATGCNATHGA | 1700 |
| RGARGTNGTCATTGATACTCAGCAGCAGGCGGCTGCGCCGCACAGCACAT | 1750 |
| CCCTGTCATTGAGCCCCTGGCAGGCAGGTGTGTATAAGCTGCGGTAAtca | 1800 |
| cctgggggattgatgacaagttccccagacaatagagttttccaggtctt | 1850 |
| tagcactgctgtgctcagcgatagttgtgctctcctgtgacttcgtaagt | 1900 |
| gcctgtctcatggcaggcattgtcaggtcagaagccttctcaggcagcct | 1950 |
| cgagtaacagcgcccagttagcatcccctgaaagatgggggtatgtat | 2000 |
| aaattagcgttaaagaacatgaaccagccaccgtcatcttatcaaccaac | 2050 |
| aggcgagatgagctccgattcctgattcttcacattgccgttgatgcgcc | 2100 |
| tgaagcctcgcccttagggccgggaaataagcacagcatctggcgatct | 2150 |

Figure 6C

| | |
|---|---|
| cttttgccactttactgatcacatccggcctcatccatttccgggcggct | 2200 |
| tcagccatcaggagaaagggtagtggtcgtgtatatgagccaggccaaaa | 2250 |
| aaaggtgtgatatc | 2264 |

(SEQ ID NO:1)

Figure 6D

| | |
|---|---|
| MSFVTLRTGVAVALSSLIISLACPAVSAAPSLNQDIHVQKESEYPAWWKE | 50 |
| AVFYQIYPRSFKDTNDDGIGDIRGIIEKLDYLKSLGIDAIWINPHYDSPN | 100 |
| TDNGYDISNYRQIMKEYGTMEDFDSLVAEMKKRNMRLMIDVVINHTSDQH | 150 |
| PWFIQSKSDKNNPYRDYYFWRDGKDNQPPNNYPSFFGGSAWQKDAKSGQY | 200 |
| YLHYFARQQPDLNWDNPKVREDLYAMLRFWLDKGVSGMRFDTVATYSKIP | 250 |
| GFPNLTPEQQKNFAEQYTMGPNIHRYIQEMNRKVLSRYDVATAGEIFGVP | 300 |
| LDRSSQFFDRRRHELNMAFMFDLIRLDRDSNERWRHKSWSLSQFRQIISK | 350 |
| MDVTVGKYGWNTFFLDNHDNPRAVSHFGDDRPQWREASAKALATITLTQR | 400 |
| ATPFIYQGSELGMTNYPFRQLNEFDDIEVKGFWQDYVQSGKVTATEFLDN | 450 |
| VRLTSRDNSRTPFQWNDTLNAGFTRGKPWFHINPNYVEINAEREETREDS | 500 |
| VLNYYKKMIQLRHHIPALVYGAYQDLNPQDNTVYAYTRTLGNERYLVVVN | 550 |
| FKEYPVRYTLPANDAIEEVVIDTQQQAAAPHSTSLSLSPWQAGVYKLR | 600 |

(SEQ ID NO:2)

| Gene | Putative sucrose inducible promoter | |
|------|------|------|
| KIS | -55TTTTCTTTAATAACAATT-37 | SEQIDNO3 |
| RolC | -113ATTAATTAATAAATTTGT-96 | SEQIDNO29 |
| PI-II | -867ATTAATTATTATTTTTCC-850 | SEQIDNO30 |
| StPS20 | -183ATTATATAATACTAATAA-166 | SEQIDNO31 |
| CHSA | -351ATTATGTCATAAATTCTA-334 | SEQIDNO32 |
| gSPOA1 | -970CTTAATTTACTAATTTGG-953 | SEQIDNO33 |

Figure 7.

| Enzyme | Putative sucrose binding site | |
|---|---|---|
| SIM1 | $^{193}$ V-D-G-W-R-M-D-V-I-G-S-I $^{204}$ | SEQIDNO34 |
| SIM2 | $^{192}$ V-D-G-W-R-M-D-V-I-G-S-I $^{203}$ | SEQIDNO41 |
| TPH | $^{196}$ I-D-G-F-R-L-D-V-I-N-L-I $^{206}$ | SEQIDNO35 |
| GG | $^{188}$ I-G-G-F-R-M-D-V-I-D-L-I $^{199}$ | SEQIDNO36 |
| DSRS | $^{545}$ F-D-G-I-R-V-D-A-V-D-N-V $^{556}$ | SEQIDNO37 |
| DSRA | $^{284}$ F-D-G-Y-R-V-D-A-V-D-N-V $^{291}$ | SEQIDNO38 |
| GTFB | $^{445}$ F-D-S-I-R-V-D-A-V-D-N-V $^{456}$ | SEQIDNO39 |
| GTFC | $^{471}$ F-D-S-I-R-V-D-A-V-D-N-V $^{482}$ | SEQIDNO39 |
| GTFD | $^{463}$ F-D-G-V-R-V-D-A-V-D-N-V $^{474}$ | SEQIDNO40 |
| GTFJ | $^{472}$ F-D-G-I-R-V-D-A-V-D-N-V $^{483}$ | SEQIDNO42 |
| KIS | $^{321}$ F-D-L-I-R-L-D-R-D-S-N-E $^{332}$ | SEQIDNO4 |

Figure 8.

BACTERIAL ISOLATES OF THE GENUS KLEBIELLA, AND AN ISOMALTULOSE SYNTHASE GENE ISOLATED THEREFROM

CROSS-REFERENCE TO RELATED APPLICATION

The present application is a national stage filing under 35 U.S.C. §371 of PCT/SG00/00023, filed on 15 Feb. 2000.

BACKGROUND OF THE INVENTION

1. Field of the Invention

This invention relates to the fields of bacterial molecular biology and recombinant DNA technology.

2. Description of the Related Art

Isomaltulose (6-O-α-D-glucopyranosyl-D-fructofuranose) is a reducing sugar with physical properties and taste very similar to sucrose. It is a structural isomer of sucrose found naturally in honey (Sporns et al., 1992). Isomaltulose has been regarded as an alternative to sucrose with several attractive features: (1) it resists metabolism by cariogenic oral streptococci and does not cause dental decay (Minami et al., 1990); (2) its ingestion leads to very small effects on the concentrations of glucose and insulin in blood, indicating potential as a parenteral nutrient acceptable both to diabetics and non-diabetics (Kawai, et al., 1989); (3) unlike sucrose, it is not fermented by most bacteria and yeasts and is more stable in acid solutions—these properties of isomaltulose facilitate the maintenance of sweetness and taste in fermented foods and beverages (Takazoe, 1989; Schiweck et al., 1991); (4) it does not possess hydroscopic properties like sucrose or lactose—isomaltulose-containing foods are more stable than those containing sucrose (Takazoe, 1989); (5) it selectively promotes bifidobacteria growth among human intestinal microflora (Mizutani, T. 1989). Evidence is accumulating that bifidobacteria are helpful for maintenance of human health and slowing the aging process (Mitsuoka, T. 1990). In Japan isomaltulose has been widely used as a sugar substitute in food (Takazoe, 1989). Biochemical conversion of sucrose for the production of isomaltulose has reached a scale of more than 10,000 tons annually worldwide (Kunz, 1993).

Isomaltulose is also a raw material for the synthesis of surfactants and polymers. With an annual production of around 110 million tons, sucrose is the world's most abundantly produced renewable organic compound. However, because of the acid instability of its intersaccharidic bond and its lacking of specific chemical reaction possibilities, the utility of sucrose as a raw material for the chemical industry has been very limited (Kunz, 1993). Isomaltulose, the reducing isomer of sucrose, on the other hand, can be specifically oxidized and derivatised for production of different chemical products. Isomaltulose has been successfully used for the production of polyamides and polyureas (Kunz, 1993).

Several bacterial species are known to be able to convert sucrose into isomaltulose. U.S. Pat. No. 4,359,531 describes a process for the production of isomaltulose, consisting of immobilizing whole cell or solvent extracts of whole or disrupted cells of *Erwinia rhapontici*. About 70-95% of sucrose was converted to isomaltulose products. U.S. Pat. No. 4,390,627 describes a method for immobilization of the sucrose mutase enzyme from *Protaminobacter rubrum* for production of isomaltulose. U.S. Pat. No. 4,670,387 describes a fermentation process to produce isomaltulose using immobilized cells of *Erwinia rhapontici, Protaminobacter rubrum, Serratia plymuthica, Esevinia carotovora* var *atroseptica, Erwinia dissolvens, Serratia merscescens*. Again about 70-95% of sucrose was converted. U.S. Pat. No. 4,857,461 discloses a continuous process for the enzymatic preparation of isomaltulose by immobilized crude enzyme from *Protaminobacter rubrum, Serratia plymuthica*, and *Erwinia carotovora*. U.S. Pat. No. 5,229,276 and No. 5,336,617 describe a process for preparing trehalulose and isomaltulose with immobilized cells of *Pseudomonas mesoacidophila* and *Agrobacterium radiobacter*.

A single enzyme, isomaltulose synthase (EC 5.4.99.10), is responsible for converting sucrose to isomaltulose. Although several groups of bacteria can convert sucrose to isomaltulose, yields of isomaltulose in the converted products were variable, ranging from 8% to 86% (Tsuyuki et al., 1992; Nagai et al., 1994; Huang et al., 1998). Moreover, these isomaltulose producing strains not only transform sucrose to isomaltulose and trehalulose but also produce about 2-7% of glucose as by-products (McAllister et al., 1990; Tsuyuki et al., 1992; Huang et al., 1998). This is a considerable industrial problem because elaborate purification procedures are necessary to remove these contaminating compounds (Sugitani et al., 1993, U.S. Pat. No. 5,229,276). Some strains are even capable of hydrolysis of isomaltulose into glucose and fructose.

More recently, U.S. Pat. No. 5,786,140 disclosed isolation of genes of sucrose isomerase from several organisms. By using a DNA probe based on the amino acid sequence deduced from the N-terminus of purified sucrose isomerase, the genes for sucrose isomerase were cloned from Protaminobacter rubrum, and *Enterobacter* sp. Partial DNA sequences for sucrose isomerase were further isolated from *E. rhapontici* and *P. mesoacidphila* by utilizing PCR.

BRIEF SUMMARY OF THE INVENTION

Bacterial isolates and enzymes capable of high efficiency production of isomaltulose are of considerable interest for biotechnology applications and for further understanding of enzymatic mechanisms. In the present invention a pure culture of a new bacterial isolate is provided, identified taxonomically as *Klebsiella singaporensis*. This bacterial isolate is capable of high efficiency enzymatic conversion of sucrose to isomaltulose.

The present invention further encompasses a process for the production of isomaltulose using immobilized cells of *K. singaporensis*. In contrast to those disclosed in the prior art, the process is highly efficient, converting more than 99% of sucrose to products which consist of more than 87% of isomaltulose and less than 1% of glucose. A new gene encoding sucrose isomerase from *K. singaporensis* has been cloned by a functional cloning approach, which shows a high level of similarities to, but differs in several amino acids from, the sucrose isomerase from *Enterobacter* sp.

BRIEF DESCRIPTION OF THE DRAWINGS

FIG. 1 is an electron micrograph of the negatively stained cell of strain *Klebsiella singaporensis* grown on sucrose medium.

FIGS. 6A-6D show the nucleotide and protein sequences of the KIS gene. FIGS. 6A-6C is the nucleotide sequence (SEQ ID NO:1) of the KIS gene of *Klebsiella singaporensis*. The DNA sequences of upstream and terminator regions are shown in initialized fonts, while the DNA sequences in the ORF are indicated by normal fonts. The putative potential ribosome binding site (SD) is underlined. The putative sucrose inducible region in the upstream is indicated by double underlines. A sequence homologous to the helix-loop-helix binding site is boxed. Bold fonts indicate the factor-independent termination sites in the downstream. FIG. 6D shows the deduced amino acid sequence (SEQ ID NO:2) of KIS protein. The putative sucrose binding site is underlined.

FIG. 7 is the homologous sequence associated with the AT-rich sequence of the putative sucrose-inducible promoter in the KIS gene. Kis is the gene for isomaltulose synthase from *Klebsiella singarporesis* LX3. Numerals are distance (bp) from the transcription site, except the kis where the numbers are the distance (bp) from the translational initiation site ATG.

FIG. 8 details a comparison of amino acid sequence in the putative sucrose binding site between kis and other enzymes which use sucrose as a substrate. The numbers represent the position from the N termini of the enzymes.

DETAILED DESCRIPTION OF THE INVENTION

Two pure isolates (LX3 and LX21), that can convert sucrose into isomaltulose, were isolated from soil samples of the Republic of Singapore and from the root zone of sugarcane.

According to the description of the genus *Klebsiella* previously published(Orskov, 1984), this genus has the following morphological characteristics: negative reaction in Gram stain and oxidase, facultatively aerobe, rod-shape, non-motion, positive reaction in V.P. test and producing capsulate. These characteristics are consistent with those of the isolates of the present invention, suggesting that strain LX3 and LX21 should belong to the genus *Klebsiella*.

The isolates of the present invention can be distinguished from all of these known species of the genus *Klebsiella* by its phenotypic characteristics, including indole production, growth at 10° C., gas production from lactose, and methyl red test (Table 1). The difference of the isolates from the closely related species *Klebsiella pneumoniae* is that the latter can produce gas from lactose at 44.5° C. but can not grow at 10° C.

TABLE 1

Comparison of phenotypic characteristics of the two new isolates and related species.

| Isolates | LX3 | LX21 | K. pneumoniae | K. oxytoca | K. ozaenae | K. rhinoschleromatis | S. liquefaciens |
|---|---|---|---|---|---|---|---|
| Indole production | − | − | − | − | + | − | − |
| Gas production from Lactose at 44.5° | − | − | + | − | + | + | |
| Growth at 10° C. | + | + | − | + | − | − | + |
| M.R. | − | − | − | − | + | + | + |
| V.P. | + | + | + | + | − | − | − |
| Growth on cellobiose | + | + | + | + | + | + | − |
| Acid from lactose | + | + | + | | (+) | − | − |

A phylogenetic analysis indicated that the strain of the present invention clusters with genus *Klebsiella*. The closest relatives are *K. pneumoniae, K. rhinoscleromatis, K. ozaenae* and *S. liquefaciens*. It has been proposed that strains sharing less than 97% similarity usually do not belong to the same species (Stackebrandt and Goebel, 1994). The similarity of 16s rRNA sequences between strain LX3 and *Klebsiella pneumoniae* was only 94.8%.

Figure 3:
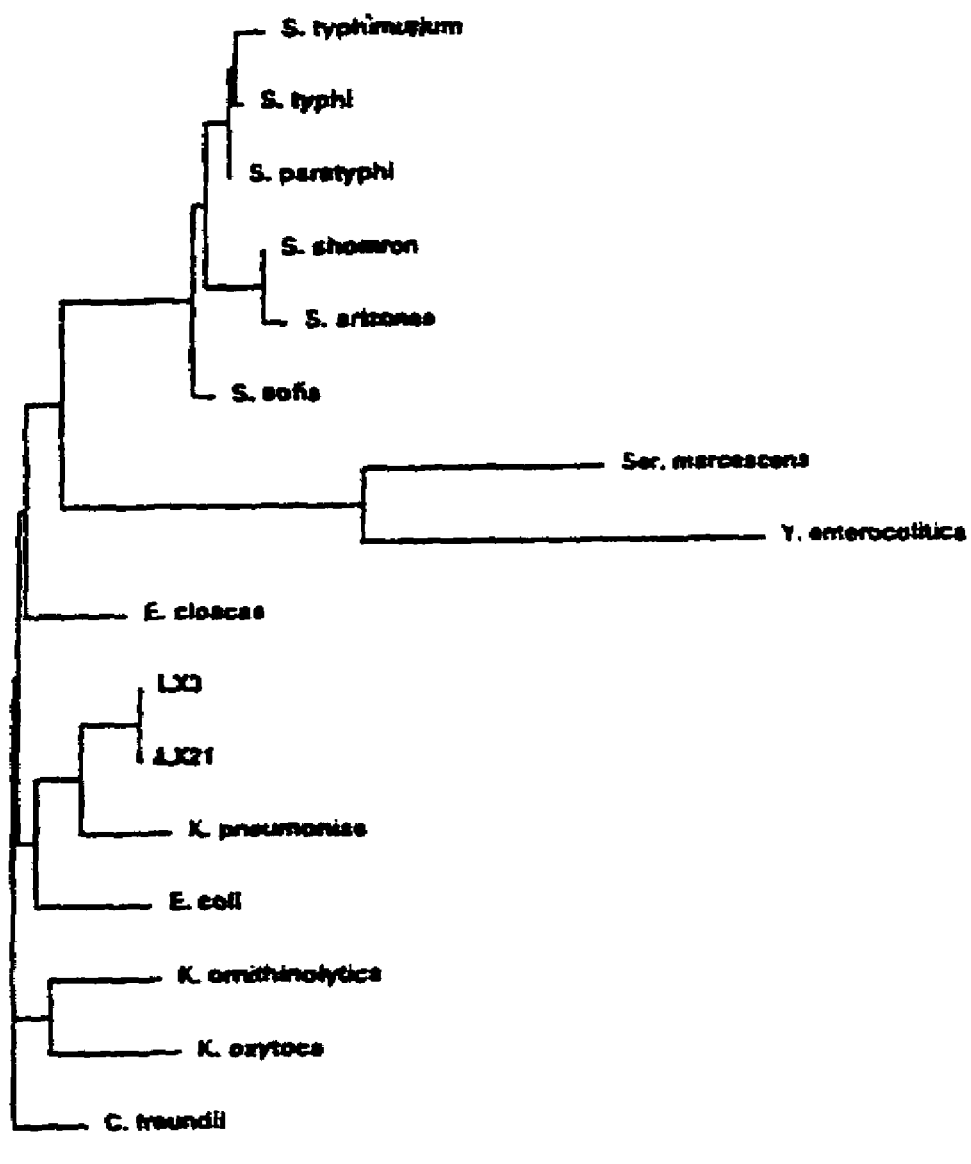
FIG. 3 details the phylogenetic position of *Klebsiella singaporensis* among selected bacteria belonging to the family of Enterobacteriaceae based on partial rpoB gene sequence data analysis. The tree was generated by the neighbor-joining method.

There are many similar phenotypic properties among the classified species of genus *Klebsiella*. To overcome this classification problem, phylogenetic analysis based on rpob gene sequences was also carried out. It has been found that levels of divergence between the rpoB sequences of different strains in the family *Enterobacteriaceae* were markedly higher than those between their 16s rRNA genes (Mollet et al., 1997). The intraspecies comparison exhibited 98-100% of similarity among enteric strains, whereas a 2-21.9% difference occurred interspecies. As shown in FIG. 3, analysis of rpoB gene sequences enabled an estimation of the phylogenetic position of the strains of the present invention. Although the rpoB gene analysis showed the similar phylogenetic position of the isolates to that of 16s rRNA sequence analysis, it is noteworthy that the rpoB gene divergence of the strains of the present invention from the other related strains is higher than that of 16s rRNA sequences. The range of similarities among strains tested is from 88.3% to 94.9%.

According to the physiological and phylogenetic characteristics of strains LX3 and LX21, it is apparent that these strains cannot be assigned to any previously recognized bacterial species. It is therefor proposed that strain LX3 and LX21 should be placed in a new species, *Klebsiella singaporensis* sp. nov. The type strain for this new species is designated LX3$^T$.

Isomaltulose synthase catalyzes the conversion of sucrose into both isomaltulose and trehalulose (Cheetham et al., 1982). The *K. singaporensis* strains LX3$^T$ (type strain)and LX21 convert sucrose into isomaltulose (87.3%), a small amount of trehalulose (11.6%) and trace amount of glucose (<1%). In comparison to other isomaltulose-producing strains (McAllister et al., 1990; Tsuyuki et al., 1992; and Huang et al., 1998), the isolates of the present invention produced more isomaltulose and less trehalulose from sucrose medium, and especially much less glucose.

The isomaltulose synthase enzyme activity of *K. singaporensis* is significantly higher than that of *Erwinia rhapontici* ATCC 29283 and *Serratia plymuthica* ATCC 15928, two strains known for isomaltulose production (Bucke and Cheetham, 1987, U.S. Pat. No. 4,670,387; Egerer et al., 1989, U.S. Pat. No. 4,857,461). Under the same growth conditions, the isomaltulose synthase activity of *K. singaporensis* is 43% and 19% higher, respectively, than that of *Erwinia rhapontici* ATCC 29283 and that of *Serratia plymuthica* ATCC 15928. This explains the very high sucrose conversion rate of *K. singaporensis*. The immobilized cells of *K. singaporensis* provide almost complete conversion of sucrose (99.7%), whereas the conversion rate of other known strains was up to 95% only (Bucke and Cheetham, 1987, U.S. Pat. No. 4,670,387). This novel bacterial strain, *K. singaporensis*, could have a significant industry potential for efficient production of isomaltulose.

Interestingly, the isomaltulose synthase (KIS) in strain *K. singaporensis* is not constitutively expressed. It is significantly induced by fructose containing carbohydrates, including fructose, sucrose, raffinose, and isomaltulose. Among them, sucrose is the most effective inducer, followed by raffinose and fructose. Only low, or no enzyme activity has been detected when other sugars were used as a carbon source. This is different from the previously reported isomaltulose synthase, which is basically constitutively expressed (Huang et al., 1998).

The kis gene encoding isomaltulose synthase from *Klebsiella singaporensis* has been cloned and characterized and found to have the nucleic acid sequence shown in FIGS. 6A-6C (SEQ ID NO. 1). The present invention encompasses nucleic acid sequences within the scope of the degeneracy of the genetic code that encoded essentially the same amino acid sequence (SEQ ID NO:2) encoded by SEQ ID NO:1. The gene encodes a peptide of 598 amino acids with a calculated molecular mass of 69.94 kDa. Sequence comparison indicates that it is highly similar to but different from the sucrose isomerase cloned from *Enterobacter* sp. strain SZ62. There are 3 amino acid differences at the C-terminal region.

A functional cloning method for isolating the DNA encoding the KIS protein can be stated as follows: (a) prepare a gene bank from a donor organism that contains a DNA sequence coding for an isomaltulose biosynthesis activity in a suitable host organism, (b) screen the clones of interest from the gene bank by their enhanced reducing sugar content, and (c) isolate the clones which contain a DNA coding for a protein with isomaltulose biosynthesis activity. In a preferred embodiment, *E. coli* is used as the host organism for the gene bank of step (a), most preferably an *E. coli* strain that does not produce significant amounts of reducing sugar with the time frame needed to perform the steps (a)-(c), above.

A putative promoter sequence in the upstream of ORF of the kis gene has been identified. The promoter activity has been confirmed in *E. coli*, where it directs inducible expression of the kis gene in the presence of sucrose or fructose. The putative AT-rich sucrose responsive region ($^{-54}$TTTTCTTTAATAACAATT$^{-37}$) [SEQ ID. 3] is found at −10 region by comparison with other sucrose-responsive regions (Yokoyama et al., 1994).

The isomaltulose synthase belongs to the family of glucosyltransferases. Comparison of the deduced amino acid sequence of the kis gene suggests the existence of a potential sucrose-binding site, $^{321}$F-D-L-I-R-L-D-R-D-S-N-E$^{332}$ [SEQ ID NO. 4]. It has been established that aspartic acid residues are important for the binding of the glucosyl group of sucrose and its derivatives. Changing Asp to Asn in the sucrose-binding site in glucosyltransferases resulted in reduced or completely inhibited enzyme activity, indicating the role of carboxyl groups in the catalytic site (Mooser et al., 1991; Kato et al., 1992; Monchois et al., 1996, 1997). It seems likely that, by comparison, the Asp-327 in the KIS enzyme is responsible for the catalytic binding of sucrose in isomaltulose biosynthesis. The role of a second highly conserved amino acid, i.e. Arg-325, in the substrate binding and catalysis, has not yet been established.

The isomaltulose synthase of the present invention can be expressed in any number of cell types, such as bacterial, plant, mammalian, insect or fungal cells, and the present invention encompasses prokaryotic and eukaryotic cells transformed to express KIS. In one preferred embodiment, the kis gene is transferred into a bacterial cell, such as *E. coli*, by conventional methods, and the KIS enzyme expressed therein. Such a transformed bacterial cell line can be used to produce isomaltulose in fermentation culture. In another preferred embodiment, the kis gene is transferred into a plant cell. Such a transformed plant cell could be used to produce isomaltulose in culture, or regenerated by conventional methods into a transgenic plant expressing the kis gene in its tissues, leading to the production of isomaltulose through the conversion of sucrose. Such a plant would be a rich source of isomaltulose. Preferred plants for use in this embodiment are sugarcane, maize, watermelon and sugarbeet.

Cell transformation can be accomplished using conventional means, such as transformation by an appropriate expression vector that is propagated in the host cell (such as a plasmid), by mechanical means (e.g., particle bombardment, microinjection), or by other means known in the art, such a liposome fusion or electroporation. A preferred embodiment for the transformation of plants and plant cells is an *Agrobacterium tumefaciens* Ti plasmid vector, of which there are numerous examples in the literature (e.g., U.S. Pat. Nos. 4,940,838, 4,762,785 and 5,068,193). Transformation with a Ti plasmid vector can be achieved via *Agrobacterium*-mediated transformation, or by any other means that effects the transferral of Ti plasmid into the target cell. In a preferred embodiment, the kis gene is incorporated into an expression vector that propagates in a prokaryotic or eukaryotic cell, and the present invention encompasses transformed prokaryotic and eukaryotic cells harboring such vectors. An appropriate expression vector would comprise the kis coding sequence and a promotor active in the host cell that causes expression of the kis coding sequence, as well as sequences necessary for the maintenance and/or propagation of the vector in the host cell. Additionally, the vector may comprise sequences that lead to the stable insertion of the kis gene into the host cell genome, for example the Ti plasmid border regions (c.f. U.S. Pat. Nos. 4,762,785 and 5,068,193), or any region of homology that can lead to cross-over or insertion events with the host genome.

In another embodiment, the kis gene is fused to a signal peptide sequence. Signal peptides effect the targeting of the expressed peptide to a particular cellular local, such as the vacuole (Bednarek and Raikhel, 1991; Matsuoka and Nakamura, 1991), the chloroplast (Van den Broeck et al., 1985), the endoplasmic reticulum (Borisjuk et al., 1999), or the cell membrane (Okamoto et al., 1991). In a preferred embodiment, the kis gene is fused to a vacuole-targeting signal peptide sequence. In still another embodiment, the kis gene is linked to a membrane attachment domain coding sequence, which would be important for enzyme stability (Hsu et al., 1993; Okamoto et al., 1991).

EXAMPLE 1

Isolation, Purification and Characterization of Isomaltulose Producing Bacteria *Klebsiella singaporensis* sp. nov.

Soil samples collected at Woods Park of Clementi, Singapore, or from the root zone of sugarcane, and the tissue of various over-ripe tropical fruits and sugarcane were suspended in sterilized saline water and spread over sucrose agar plates in different dilutions. The sucrose agar medium used for the screening of bacteria producing isomaltulose, contained (per 1000 ml): 40 g sucrose, 5 g yeast extract, 0.5 g $MgSO_4H_2O$, 0.7 g $KNO_3$, 1 g $K_2HPO_4$, 0.5 g $NH_4Cl$, 1 g NaCl, 20 g agar, adjusted pH to 7.0 with 1 N NaOH.

Isolation and purification of isomaltulose-producing bacteria: All plates were incubated at 30° C. for 24 h. A portion of each single colony on the sucrose agar plate was transferred to a new sucrose agar plate for further purification, and another portion was inoculated into SPY medium overnight. SPY medium was composed of (per 1000 ml) 40 g sucrose, 10 g peptone and 4 g yeast extract (pH 7.0).

Bacterial isolates from different samples were purified into homogeneous single-colony cultures by repeating streaking on the SPY plates. The purified bacterial isolates were screened for production of reducing sugars using sucrose as a sole carbon source. The bacterial isolates capable of producing reducing sugars in high yield were further tested for isomaltulose and glucose production. Two bacterial isolates (LX3 and LX21) capable of efficient production of isomaltulose with trace amounts of glucose by-product were selected for further study. These two isolates were originally isolated from the soil sample close to the root of sugarcane and from soil samples at Woods Park of Clementi of Singapore, respectively.

Preparation of crude isomaltulose synthase and enzyme assay: After incubation overnight in SPY medium, the cells and supernatant were collected respectively by centrifugation at 14000 rpm for 10 min. The supernatant was kept at 4° C. for the detection of reducing sugars by the DNS method (Miller, 1959), and isomaltulose by thin-layer chromatography (Schwimmer and Bevenue, 1956), assays described infra. The cell-pellet was washed three times with deionized water and suspended in original volume of 0.1M citrate-phosphate buffer (pH 6.6). The resuspended bacterial cells were divided into two aliquots. One aliquot was used directly for enzyme assay as a whole cell fraction. The cells of the other aliquot were broken by sonication, the crude protein extract and the cell-debris fractions were separated by centrifugation at 14000 rpm. The cell-debris fraction was washed three times and resuspended in the same buffer for enzyme assay.

The enzyme activity was determined by incubating a mixture of 450 µl of 4% sucrose in 0.1 M citrate-phosphate buffer (pH 6.6) and 50 µl of enzyme preparation or bacteria suspension at 37° C. for 15 min. The reducing sugars formed were determined by the DNS method. One unit of isomaltulose synthase activity is defined as the amount of enzyme that can convert sucrose into one pmol of reducing sugar in a minute at the conditions specified above.

For determination of the enzyme activity in *E. coli* host cells, the same conditions were applied except that the bacteria were grown in LB medium supplemented with different concentrations of sucrose as indicated, bacterial suspension culture was doubled to 100 µl and sucrose solution was reduced correspondingly to 400 µl and the reaction time was increased to 30 minutes.

Detection of bacteria introducing isomaltulose by thin-layer chromatography: The 0.5 µl of supernatant of culture, in which reducing sugars can be detected by the DNS method, was spotted on TLC plates (Silica Gel on polyester for general-purpose, Aldrich) and developed. The solvent system was ethylacetate-acetic acid-water (4:3:0.8 by volume). The spots were visualialized with the diphenylamine-aniline-phosphoric acid reagent (Schwimmer and Bevenue, 1956) at 80° C. for 5 min. The presence of isomaltulose is indicated by a typical green-yellow color spot, the isomaltulose from Sigma was used as a standard control.

After sonication no isomaltulose synthase activity was detected in the supernatant fraction and the activity was only found in the cell-pellet fraction, which was not changed by prolonged sonification. The isomaltulose synthase activity of cell-pellet fraction (19.2 U/ml) is almost identical to that of whole cell fraction (20.1 U/ml). The results suggest that the isomaltulose synthase is a cell wall-bound enzyme.

Morphology: The cultures were grown on sucrose agar for 24 h at 30° C. and examined with a phase-contrast microscope and transmission electron microscope (TEM). For transmission microscopy, a centrifuged cell pellet was fixed with 5% (wt/vol) glutaraldehyde and 1% (wt/vol) osmium tetroxide. Ultrathin sections of the sample embedded in epoxy resin were prepared with an ultramicrotome, stained with uranyl acetate and lead citrate, and examined with a model JEM-1200 EX transmission electron microscope. Cellular morphology after Gram staining was also checked by light microscopy, and the morphology of fixed specimens was compared to that of living cells.

Strains LX3 and LX21 are Gram-negative, non-motile, straight rods with round ends, appearing singly and sometime in pairs. The cells are of 0.6-0.8 µm in diameter and 0.9-2.0 µm in length. Endospores have not been observed. The size and shape of cells grown on sucrose medium was monitored and is illustrated in FIG. 1. Colonies of these two isolates were circular, smooth, pulvinate, entire, opaque, white and viscous when tested with needle.

Physiological and Biochemical Characterization: Basal medium used for physiological and biochemical characterization of bacterial isolates in taxonomic work consisted of (per 1000 ml) 0.5 g $MgSO_4H_2O$, 0.7 g $KNO_3$, 1 g $K_2HPO_4$, 0.5 g $NH_4Cl$, 1 g NaCl, and pH 7.0-7.2, carbon source was added as specified. The liquid cultures of bacterial isolates were incubated at 30° C. with reciprocal shaking.

Gram staining characteristics were determined using the Hucker method as described (Doetsch, 1981). Oxidase activity was determined by oxidation of 1% (wt/vol) tetramethyl-p-phenylene-diamine on filter paper, and catalase activity was detected by bubble formation in a 3%. (wt/vol) hydrogen peroxide solution after incubation in SPY medium for 18-48 h (Smibert and Krieg, 1981). The media used to evaluate utilization of various substrates for growth were prepared by adding 0.2% (wt/vol) of each substrate to the basal medium. Gelatin hydrolysis (method 1), indole production (method 2), hydrogen sulfide production (method 2), nitrate reduction and hydrolysis of starch, casein and agar were tested by using the methods previously described (Smibert and Krieg, 1981). Acid production from carbohydrates was determined in basal medium supplemented with various carbohydrates as described (Smibert and Krieg, 1981).

Growth of bacterial isolates from 5° C. to 60° C. was determined by inoculation of fresh cultures of isolates onto sucrose agar plates and incubation at different temperatures respectively for 10 days.

The physiological and biochemical properties are shown in Table 2. The two strains show catalase and urease activities but do not have oxidase, nitrate reductase and lipase activities. Both strains can not hydrolyze gelatine, starch and cellulose. Strain LX3 cannot hydrolyze casein, while LX21 can degrade casein. The Voges-Proskauer test is positive but Methyl Red reaction is negative. LX3 and LX21 were facultative, anaerobic and capsulated. They both can use citrate and glucose as a sole carbon source and produce acid and gas from all the tested carbon sources, including glucose, sucrose, lactose, trehalulose, maltose, fructose, mannitol, glycerol, inositol, mannose, galactose and sorbitol. The nitrogen sources such as peptone, tryptone, yeast extract, beef extract, casein hydrolysate, $KNO_3$, $(NH_4)_2SO_4$ can support the growth of the isolate, whereas urea can not. There are no special growth factor requirements of the isolates.

TABLE 2

Characteristics of bacterial isolates LX3 and LX21

| Isolates | LX3 | LX21 |
|---|---|---|
| Straight Rod | + | + |
| Round-end | + | + |
| Diameter | 0.6-0.8 | 0.6-0.8 |
| Length | 0.9-2.0 | 0.9-2.0 |
| Occurrence | | |
| Single | + | + |
| Pair | Sometime | Sometime |
| Capsules and slime layer | + | + |
| Gram | − | − |
| Cyst and Microcyst | − | − |
| Coccoid body | − | − |
| Endospore | − | − |
| Motility | − | − |
| Facultative anaerobic | + | + |
| Catalase | + | + |
| Oxidase | − | − |
| Urease | + | + |
| Lecithinase | − | − |
| Lipase | − | − |
| Citrate utilization | + | + |
| Hydrolysis of | | |
| Gelatine | − | − |
| Starch | − | − |
| Cellulose | − | − |
| Casein | − | − |
| Glucose as carbon source | + | + |
| Catabolism | Fermentation | Fermentation |
| $H_2S$ production from | | |
| Cysteine | + | + |
| Thiosulfate | − | − |
| TSI | − | − |
| M.R. | − | − |
| V.P. | + | + |
| Nitrate reduction | − | − |
| Indole production | − | − |
| Gas production | + | + |
| Acid | + | + |

These characteristics allow grouping of strains LX3 and LX21 to the genus *Klebsiella*. The closest members are *K. oxytoca* and *K. pneumoniae*. But strains LX3 and LX21 differ from *K. oxytoca* in indole production and differ from *K. pneumoniae* in their abilities to grow at 10° C. and to produce gas from lactose at 44.5° C. (Table 1).

The distinct physiological, biochemical properties, and as well as DNA sequence differences examined in Example 3, indicate that isolates should be classified as a new bacterial species within the genus *Klebsiella*, i.e. *Klebsiella singaporensis*. The type strain is $LX3^T$.

Description of *Klebsiella singaporensis* sp. nov.: *Klebsiella singaporensis* (sin.ga.po.ren'.sis M.L. gen. n. singaporensis of Singapore; pertaining to Singapore, a name of a country in Asia).

Gram-negative facultatively anaerobic straight rod with round ends. Non-motile and capsulated. Not endospore forming. Cells range from 0.6-0.8 μm in diameter to 0.9-2.0 μm in length and occurs singly and sometimes in pairs. Colonies are circular, smooth, pulvinate, entire, opaque, white and viscous when grown on sucrose agar plates. Catalase and urease are produced, oxidase, and lipase are not produced. Voges-Proskauer test is positive and Methyl Red reaction is negative. Nitrate is not reduced. Does not ferment gelatin, starch, cellulose and casein. There are no special growth factor requirements. Citrate and glucose can be used as a sole carbon source. Lack of production of $H_2S$. Acids and gas are produced from glucose, sucrose, lactose, trehalulose, maltose, fructose, mannitol, glycerol, inositol, mannose, galactose and sorbitol. Optimum temperature 30° C. and optimum pH 7.0. The G+C content of DNA is 56.5 mol %. The type strain is $LX3^T$.

EXAMPLE 2

Immobilization of *K. singarporesis* $LX3^T$ in Alginate and Production of Isomaltulose using Immobilized Cells Strain $LX3^T$ was grown in Spy medium at 30° C. for 16 h with shaking (250 rpm). Per 5 ml of bacterial culture was mixed with 100 ml of alginatic acid (2%, medium viscosity) and dropped into 0.65% (w/v) $CaCl_2$ solution with a syringe. The solution was stirred constantly and the immobilized cells were hardened gradually in the 0.65% (w/v) calcium chloride solution at 4° C. for 4 h. The immobilized cells were then incubated in SPY medium containing 0.2% (w/v) $CaCl_2$ overnight at 30° C. with shaking for increasing the bacterial cell density in the alginate particles.

The immobilized cells (100 ml) were packed in 200 ml column reactors. Sucrose solutions at different concentrations were passed through the columns with different retention times. Eluates were collected and the yield of total reducing sugar as well as isomaltulose under different conditions was determined as described above.

Production of isomaltulose by immobilized cells of *K. singaporensis*: The fresh cultures of *K. singaporensis* was immobilized in alginate gel. Table 3 shows the isomaltulose production efficiency of the immobilized cells, which were packed in 200-ml column reactors. Best sucrose conversion rate (99.7%) was achieved when 10% sucrose solution passed through the column reactor in a rate of 6 ml/min. Under these conditions, the yield of isomaltulose was 522.8 mg/min or 31 kg/h. Increments of sucrose concentration up to 20% further increased the yield of isomaltulose, but sucrose conversion rate was decreased. Higher sucrose concentration did not result in better yield.

TABLE 3

Production of isomaltulose by immobilized *S. singarporensis**

| Sucrose concentration | Retention time (ml/min) | Conversion rate (%) | Yield (mg/min)** |
|---|---|---|---|
| 10 | 2 | ND | ND |
|  | 4 | 99.7 | 348.5 |
|  | 6 | 99.7 | 522.8 |
| 20 | 2 | 98.2 | 343.3 |
|  | 4 | 96.4 | 674.0 |
|  | 6 | 72.1 | 756.2 |
| 30 | 1 | 71.8 | 188.3 |
|  | 2 | 65.4 | 342.9 |
|  | 3 | 32.7 | 357.2 |
| 40 | 1 | 67.2 | 234.9 |
|  | 2 | 65.1 | 455.2 |
|  | 3 | 34.3 | 359.7 |

*The data are means from two replicates per treatment.
**Yield of isomaltulose was converted according to the detected proportion of isomaltulose in total reducing sugar 87.4%).

Determination of products ratio: Washed bacterial cells of strain LX3 were incubated with 4% sucrose in 0.1 M citrate-phosphate buffer (pH 6.6) for 10 min at 37° C. The reaction was stopped immediately by heating in boiling water bath for 5 min. The supernatant of the reaction mixture was spotted onto a TLC plate and developed as described. The TLC plate fractions containing isomaltulose and trehalulose were cut and extracted with distilled water respectively. The sugar concentration was determined by the DNS method and the ratio of these two sugars was calculated.

For determination of glucose content in the reaction mixture, the concentrations of glucose and total reducing sugar of the above supernatant were analyzed respectively using the Glucose (HK) Assay Kit (Kit GAHK-20, Sigma) and the DNS method. The ratio of isomaltulose, trehalulose and glucose was determined with the above quantification data.

Enzyme and isomaltulose production: Strain LX3$^T$ was cultured aerobically in the basal medium supplemented with different sugars at the same initial concentration (1.5%, w/v) as sole carbon sources at 30° C., and the samples were removed at intervals for determination or isomaltulose synthase activity, cell mass and isomaltulose production. As shown in Table 4, the best enzyme activities were detected when sucrose, raffinose or fructose was used as sole carbon source, which is 15.12, 13.62 or 11.08 U/ml respectively. Enzyme activity lower than 1.7 U/ml was obtained when maltose, mannitol, mannose, lactose, cellobiose or melibiose was used as the carbon source. Isomaltulose was also able to induce the production of isomaltulose synthase, but the activity was only 30% of that in the presence of sucrose. Almost all the tested monosaccharides including glucose, xylose, arabinose and galactose could not induce isomaltulose synthase activity, with the exception of fructose.

TABLE 4

Effects of carbon source on isomaltulose synthase production by *K. singaporensis* LX3. The basal medium is comprised of 0.1% peptone, 0.2% yeast extract, 0.05% MgSO$_4$, 0.2% NaCl.

| Carbon source (1.5%, w/v) | Growth (OD600) | KIS activity (U ml$^{-1}$) |
|---|---|---|
| Sucrose | 1.89 | 15.1 |
| Glucose | 1.94 | 0.0 |
| Fructose | 1.82 | 11.1 |
| Raffinose | 1.96 | 13.6 |
| Isomaltulose | 1.92 | 4.5 |
| Melibiose | 1.88 | 1.6 |
| Maltose | 1.77 | 1.5 |
| Mannose | 1.84 | 0.7 |
| Lactose | 1.82 | 0.0 |
| Xylose | 1.97 | 0.0 |
| Arabinose | 1.73 | 0.0 |
| Galactose | 1.71 | 0.0 |
| Mannitol | 1.77 | 1.7 |
| Cellobiose | 1.83 | 0.0 |

Strain LX3$^T$ did not grow well when inorganic chemicals such as KNO$_3$, urea or (NH$_4$)$_2$SO$_4$ was used respectively, as a sole nitrogen source, and no isomaltulose synthase activity has been detected in the cultures (Table 5). All organic nitrogen sources tested support good growth of the strain LX3$^T$, but with varied isomaltulose synthase activities. Among them, yeast extract and tryptone are most effective in promoting induction of maximum isomaltulose synthase activities (Table 5).

TABLE 5

Effect of nitrogen source on isomaltulose synthase production by *K. singaporensis* LX3. The basal medium is comprised of 1.5% sucrose, 0.02% MgSO$_4$, 0.5% NaCl, 0.03% K$_2$HPO$_4$. The data are means from two replicates per treatment.

| Nitrogen source (0.5%, w/v) | Growth (OD$_{600}$) | Relative KIS enzyme activity (%) |
|---|---|---|
| Peptone | 1.97 | 59.2 |
| Tryptone | 2.13 | 85.9 |
| Yeast extract | 2.33 | 100 |
| Beef extract | 2.23 | 54.4 |
| Casein hydrolysate | 2.34 | 53.9 |
| KNO3 | 0.60 | 0 |
| Urea | 0.33 | 0 |
| (NH$_4$)$_2$SO$_4$ | 0.56 | 0 |

Figure 4:
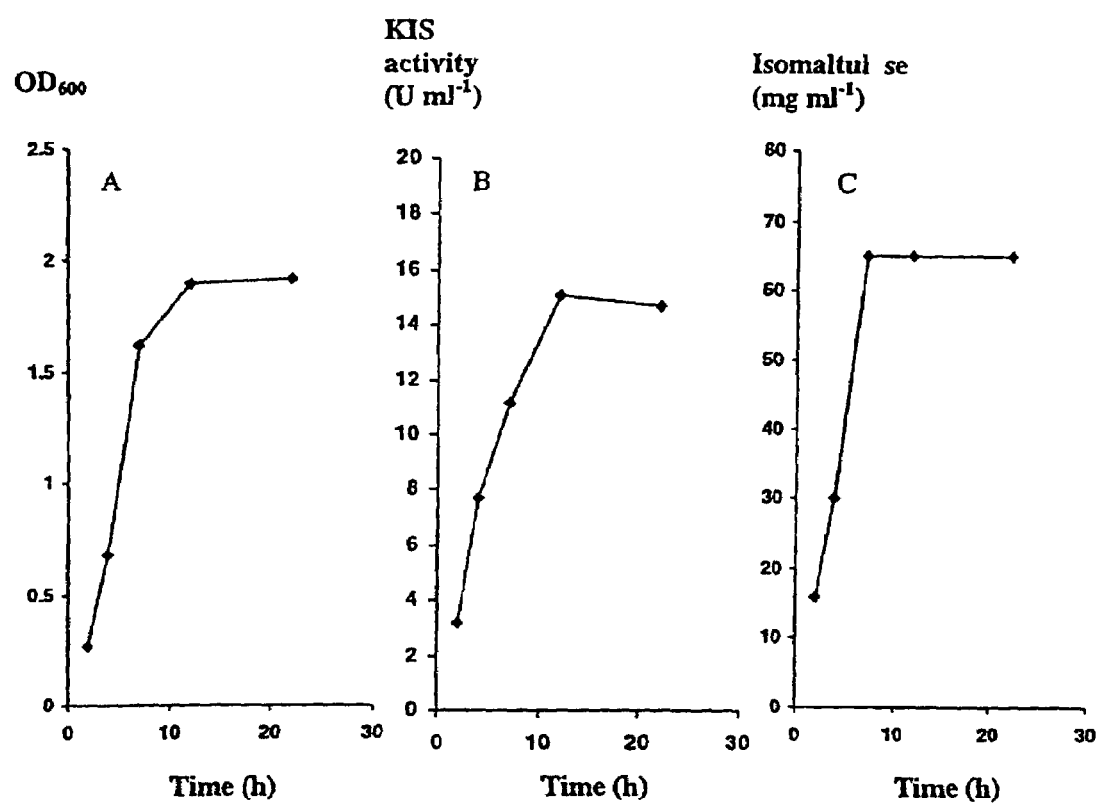
FIG. 4 shows isomaltulose production and KIS enzyme activity in *K. singaporensis* cell culture. The first graph, A, details bacterial growth over a 24 hour time period. The second graph, B, details the KIS enzyme activity in the same time period. The last graph, C, shows the isomaltulose detected in the culture medium over the same time period.

FIG. 4 shows a typical profile of isomaltulose and isomaltulose synthase productions by strain LX3$^T$. Isomaltulose production is rapid and reaches the maximum level after 7 h culture when the concentration of sugar in the medium is 10%. From 7 to 22 h, the concentration of isomaltulose in the culture is maintained basically in the same level, indicating that strain LX3$^T$ is unable to metabolize isomaltulose. It is noted that at 7 h, both bacterial growth and isomaltulose activity in the culture did not reached the maximum level, whereas isomaltulose production basically stopped. One possibility is that when sucrose concentration in the medium reaches a low level, the remaining sucrose is actively pumped into cells to support bacterial growth.

Comparison of isomaltulose synthase enzyme activities of several bacterial strains: Under the same growth conditions (SPY medium), the relative isomaltulose synthase activities of *K. singaporensis*, *Erwinia rhapontici* ATCC 29283 and *Serratia plymuthica* ATCC 15928 were determined to be 100%, 57%, and 81% respectively.

EXAMPLE 3

Manipulation, Cloning, Location and Sequence Analysis of the kis Gene

DNA manipulation: Purification of total genomic DNA, digestion of DNA with restriction endonucleases, DNA ligation, agarose gel electrophoresis and transformation of E. coli DH5α were carried out by standard procedures (Sambrook et al., 1989) or as recommended by the reagent manufacturers. Plasmid preparation was performed with the kits from Qiagen according to the manufacturer's instructions. DNA restriction fragments were isolated from the agarose gel by using a QIAEX II Gel Extraction Kit (Qiagen).

The bacterial strains and plasmids are listed in Table 6. E. coli DH5α was used as the cloning host strain. Plasmid vectors pLAFR3 and pBluescript II SK (+) were used for constructing the genomic DNA library, and for subcloning, respectively. E. coli cosmid clones and subclones where grown aerobically at 37° C. in Luria-Bertani-sucrose medium (per liter contains Bacto Tryptone 10 g, yeast extract 5 g, NaCl 10 g, and sucrose 50 g, pH 7.0). When necessary, tetracycline (12 mg/liter) or ampicillin (100 mg/liter) was added to the medium.

TABLE 6

Bacterial strains and plasmids used in this study

| Strain | Genotype or phenotype | Reference/source |
|---|---|---|
| Bacteria | | |
| K. singaporensis LX3$^T$ | Soil isolate, isomaltulose producer | This study |
| K. singaporensis LX21 | Soil isolate, isomaltulose producer | This study |
| Erw. rhapontici ATCC 29282 | isomaltulose producer | ATCC |
| S. plymuthica ATCC 15928 | isomaltulose producer | ATCC |
| E. coli DH 5α | recA1 endA1 hsdR17supE4 gyrA96 relA1 Δ(lac ZYA-argF)U169(80DLACzΔM15) | Sambrook et al. 1989 |
| Plasmids | | |
| pPLAFR3 | Cloning vector, Tc$^r$ | Lab collection |
| pBluescript II sk(+) | Cloning vector, Amp$^r$ | Stratagene |
| pPLASI164 | PLAFR3 plasmid with ~6.1 kb BamHI/BamHI fragment | this study |
| pSIBB | ~6.1 kb BamHI/BamHI fragment in pBluescript II SK(+) | |
| pSIBP | ~4.8 kb BamHI/PstI fragment in pBluescript II SK(+) | this study |
| pSICB | ~3.6 kb ClaI/BamHI fragment in pBluescript II SK(+) | this study |
| pSIBX | ~3.5 kb BamHI/XhoI fragment in pBluescript II SK(+) | this study |
| pSIEE | ~2.5 kb EcoRV/EcoRV fragment in pBluescript II SK(+) | this study |

G+C content of DNA: The guanine-plus-cytosine (G+C) content of the genomic DNA was determined by the thermal denaturation method as described (Marmur & Doty, 1962). The G+C contents of strains LX3 and LX21 were determined to be 56.5 mol % which is comparable to that of the genus Klebsiella.

16S rRNA gene sequence: The 16S rRNA gene DNA fragments of the isolates LX3$^T$ (T=type strain) and LX21 that correspond to positions 95 to 1395 of Escherichia coli 16S rRNA was amplified by PCR using purified genomic DNA and a primer pair consisting of 5'TGACGAGTGGCG-GACGGGTG-3 (forward primer) [SEQ ID NO. 5] and 5'CCATGGTGTGACGGGCGGTGTG-3' (reverse primer) [SEQ ID NO. 6]. The amplification products were purified with a QIAquick PCR purification kit (Qiagen, Germany) and were sequenced using a dRhodamine terminator cycle sequencing kit (PE Applied Biosystems) and a model 2400 Perkin Elmer GeneAmp PCR System (PE Applied Biosystems). Sequences were determined from both strands with a Perkin Elmer ABI PRISM 377 DNA sequencer. The primers used for sequence analysis were designed and shown in Table 7. Sequencing was repeated at least two times. The closest known relatives of the new isolate were determined by performing sequence database searches and the sequences of closely related strains were retrieved from GenBank and Ribosomal Database Project (RDP II) libraries. Sequences were aligned with the PILEUP program (Devereux et al., 1984) and the alignment was corrected manually. Distance matrices were produced with the DNA-DIST program of the PHYLIP package (Felsenstein, 1989) and a phylogenetic unrooted tree was constructed using the NEIGHBOR program contained in the PHYLIP package (V3.5c) (Felsenstein, 1989). The statistical signification of the groups obtained was assessed by bootstrapping (1000 replicates) using the programs SEQBOOT, DNADIST, NEIGHBOR and CONSENSE (Felsenstein, 1989).

TABLE 7

Oligonucleotide primers used for PCR amplification and sequencing of 16s rRNA gene from strains LX3 and LX21

| Primer | | Identification Sequence (5'-3') | Orientation |
|---|---|---|---|
| 1 | 16sf95 | TGACGAGTGGCGGACGGGTG [SEQ. ID NO. 7] | Forward |
| 2 | 16sr394 | CCATGGTGTGACGGGCGGTGTG [SEQ ID NO. 8] | Reverse |
| 3 | 16sf342 | TACGGGAGGCAGCAGTGGGGAATA [SEQ ID NO. 9] | Forward |
| 4 | 16sr616 | ATGCAGTTCCCAGGTTGAGC [SEQ ID NO. 10] | Reverse |
| 5 | 16sf605 | GAAATCCCCGGGCTCAACCTG [SEQ ID NO. 11] | Forward |
| 6 | 16sf798 | ACATCGTTTACGGCGTGGACTACC [SEQ ID NO. 12] | Reverse |
| 7 | 16sf893 | GGCCGCAAGGTTAAAACTCAAATG [SEQ ID NO. 13] | Forward |
| 8 | 16sr119 | CCGGACCGCTGGCAACAAAG [SEQ ID NO. 14] | Reverse |

Figure 2:
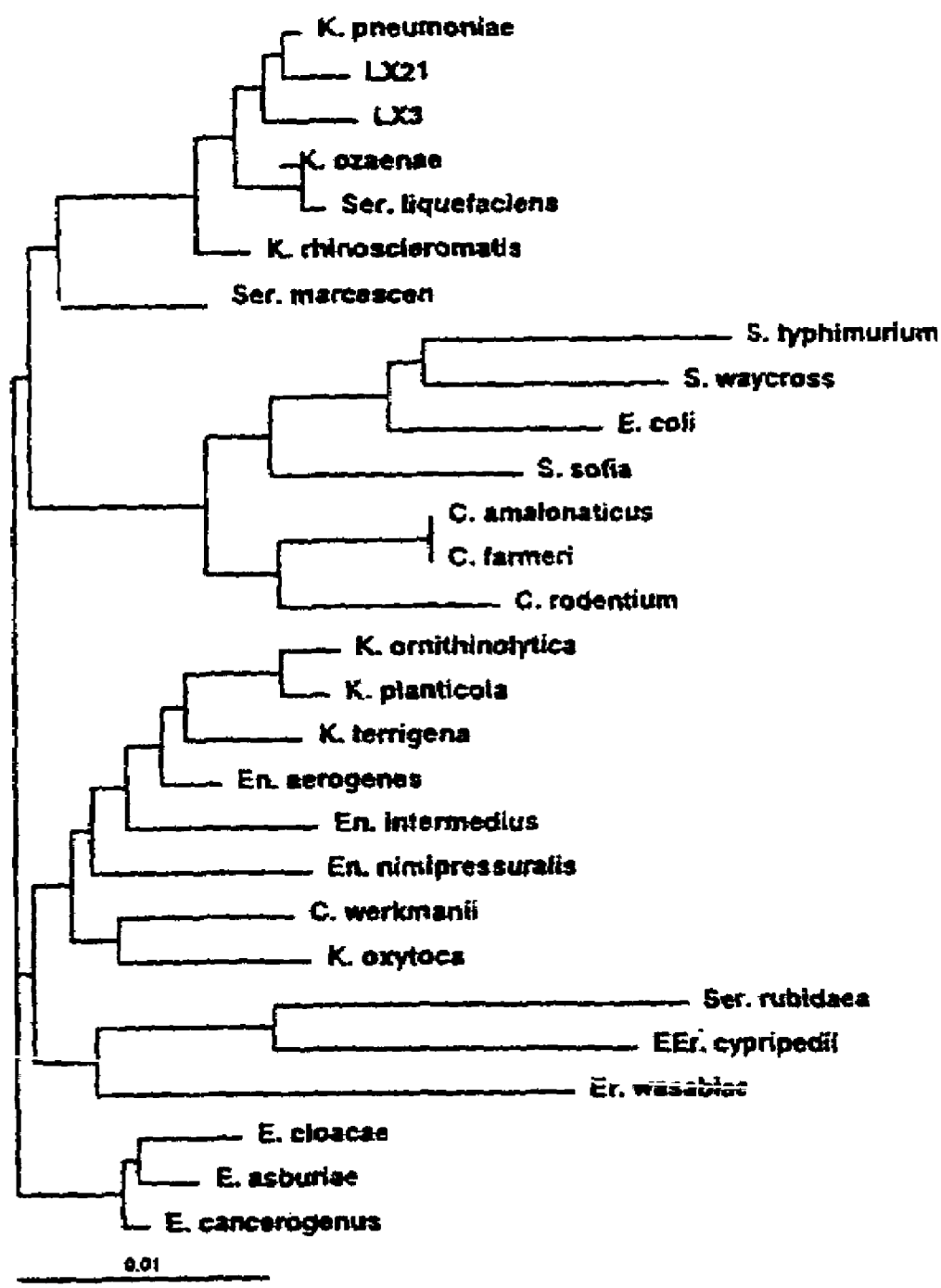
FIG. 2 shows the phylogenetic tree derived from 16S rRNA sequence data analysis, showing the position of strain *Klebsiella singaporensis*. The branching pattern was generated by the neighbor-joining method. The numbers shown next to the nodes indicate percentage bootstrap values from 1000 data sets.

The 16S rRNA gene sequence of strains LX3 and LX21 was determined. Comparison with 16S rRNA sequences available in databases revealed that strains LX3 and LX21 are closely related to the species belonging to the genus Klebsiella, and peripherally related to species of the genera Serratia and Enterobacter. The sequences of the two isolates showed high similarities with that of Klebsiella pneumoniae and the levels of sequence similarities among these strains ranged from 91.0 to 94.8%. The data set used for the construction of the phylogenetic tree contained 1282 nucleotides of each sequence as a result of elimination of gaps and ambiguous nucleotides from the sequences between positions 95 and 1395 (corresponding to that of Escherichia coli). The phylogenetic tree constructed by the neighbor-joining method is shown in FIG. 2. Strains LX3 and LX21 are closely associated with Klebsiella pneumoniae. The clustering of strain LX3 and LX21 with Klebsiella pneumoniae was supported by the results of the bootstrap analyses at a confidence level of 100%. But the two strains are different from *K. pneumoniae*; the divergence value of the 16S rRNA gene sequence of strain LX3 with that of *K. pneumoniae* is >5% (Table 8).

TABLE 8

DNA sequence similarities of 16s rRNA and rpoB genes between *Klebsiella singaporensis* sp. nov. and other representatives of the family Enterobacteriaceae

| Strains | 16s rRNA | | rpoB | |
|---|---|---|---|---|
| | GenBank No. | Similarity of 16s rRNA to *K. singa-porensis* (%) | GenBank No. | Similarity of rpoB to *K. singa-porensis* (%) |
| *Klebsiella singaporensis* | | 100 | | 100 |
| *Klebsiella pneumoniae* | Y17656 | 94.8 | U77444 | 95.0 |
| *Klebsiella rhinoscleromatis* | Y17657 | 94.7 | | |
| *Klebsiella terrigena* | Y17658 | 93.3 | | |
| *Klebsiella planticola* | Y17659 | 92.8 | | |
| *Klebsiella ozaenae* | Y17654 | 94.5 | | |
| *Klebsiella ornithinolytica* | U78182 | 93.1 | U77440 | 93.9 |
| *Klebsiella oxytoca* | Y17655 | 92.4 | U77442 | 93.6 |
| *Serratia liquefaciens* | AB004752 | 94.7 | | |
| *Serratia macescens* | M59160 | 92.2 | U77449 | 88.3 |
| *Serratia rubidaea* | AB004751 | 91.5 | | |
| *Salmonella typhimurium* | U90316 | 91.2 | X04642 | 93.4 |
| *Salmonella sofia* | X80677 | 91.5 | U77452 | 93.2 |
| *Salmonella waycross* | U92194 | 91.0 | | |
| *Citrobacter werkmanii* | AF025373 | 92.6 | | |
| *Citrobacter farmeri* | AF025371 | 93.1 | | |
| *Citrobacter amalonaticus* | AF025370 | 93.1 | | |
| *Citrobacter rodentium* | AF025363 | 91.8 | | |
| *Enterobacter cloacae* | Y17665 | 92.9 | U77435 | 94.9 |
| *Enterobacter cancerogenus* | Z96078 | 93.1 | | |
| *Enterobacter aerogenes* | AB004750 | 93.5 | | |
| *Enterobacter intermedius* | AB004747 | 92.6 | | |
| *Enterobacter asburiae* | AB004744 | 93.6 | | |
| *Enterobacter nimipressuralis* | Z96077 | 92.4 | | |
| *Erwinia wasabiae* | U80199 | | | |
| *Erwinia cypripedii* | U80201 | 91.5 | | |
| *Escherichia coli* | Z80725 | 90.8 | V00340 | 94.9 |
| *Salmonella typhi* | | | AF008577 | 92.8 |
| *Citrobacter freundii* | | | U77434 | 95.5 |
| *Salmonella arizonae* | | | U77447 | 92.0 |
| *Salmonella paratyphi* | | | U77450 | 93.0 |
| *Salmonella shomron* | | | U77451 | 92.4 |
| *Yersinia enterocolitica* | | | U77453 | 85.5 |

Partial rpoB gene DNA of strains LX3 and LX21, which represented the most variable part of the gene, were sequenced to determine the phylogenetic position of these two strains among the members of the Enterobacteriaceae family. The sequences for strain LX3 and LX21 were compared to the rpoB sequences of family Enterobacteriaceae available in database and the similarity matrix was obtained. As shown in FIG. 3, the phylogenetic position is closely related to the species belonging to the genus *Klebsiella*. The closest member is *K. pneumoniae*, but with a divergence value of 5% (Table 8).

Amplification of rpoB and sequencing: The genomic DNA of strain LX3 and LX21 coding RNA polymerase beta-subunit (rpoB) gene, corresponding to positions 1468 to 2114 of *E. coli* rpoB, was amplified by PCR using a primer pair designed with reference to the consensus regions of the published sequences for *E. coli* (GenBank V00340), *Salmonella typhimurium* (X04642), *Pseudomonas putide* (X 15849) and *Klebsiella pneumoniae* (U77443), which is 5'-CAGTTCCGCGTTGGCCTG-3' (Forward)[SEQ ID NO. 15] and 5'-CGGTTGGCGTCATCGTGTTC-3' (Reverse) [SEQ ID NO. 16]. The PCR products were purified and sequenced as described above. The phylogenetic analysis of rpoB was carried out using the same procedure and programs as that of 16S rRNA.

Cloning and Sequencing of the kis gene: A genomic DNA library was constructed by partial digestion of genomic DNA from *Klebsiella singaporensis* with BamHI, ligation into the BamHI site of the cosmid vector pLAFR3 and transfection into the *E. coli* DH5α after in vitro packaging using Gigapack II (Stratagene). The transformed *E. coli* DH5α were selected on LB agar plates containing tetracycline and incubated overnight at 37° C. The cosmid colonies were inoculated in the LB medium supplemented with sucrose, and the reducing sugar formed in the broth 24 h later was determined by using the DNS method (Miller, 1959). The presence of isomaltulose in the bacterial cultures was identified by using the thin-layer chromatography. The clones carrying the kis gene are selected and the 6.1 kb fragment was purified after digestion with BamHI. The clone pSIEE was sequenced from both strands by the chain-termination method using the ABI PRISM dRhodamine Terminator Cycle Sequencing Ready Reaction Kit (PE Applied Biosystem). The primers used for sequencing are listed in Table 9. Sequence analysis and alignment were conducted with the program DNAStar. The BLAST computer program (Altschul et al., 1997) was used for the homology search.

TABLE 9

Primers for DNA sequencing of kis gene.

| Primers | (Orientation) | Sequence |
|---|---|---|
| SI-1 | (F) | 5'-CCCGCTGGCAATATTTCTGACT3' [SEQ ID NO. 17] |
| SI-2 | (R) | 5'-CACGACCACTACCCTTTCTCCTGA-3' [SEQ ID NO. 18] |
| SI-3 | (F) | 5'-CCTCGCCTCATTTAAAGACACCAA3' [SEQ ID NO. 19] |
| SI-4 | (R) | 5'-TAGGCGCCATATACCAGAGCAG-3' [SEQ ID NO. 20] |
| SI-5 | (F) | 5'-CGTGACTATTATTTCTGGCGTGAC-3' [SEQ ID NO. 21] |
| SI-6 | (R) | 5'-CGTCGCCCGCTGAGTGAGGTAA-3' [SEQ ID NO. 22] |
| SI-7 | (F) | 5'-TAGATAACCATGACAACC-3' [SEQ ID NO. 23] |
| SI-8 | (R) | 5'-GCGGTGGCCACATCATACC-3' [SEQ ID NO. 24] |
| SI-9 | (F) | 5'-CGCCGTTTATTTATCAAGGTTCAG-3' [SEQ ID NO. 25] |

TABLE 9-continued

Primers for DNA sequencing of kis gene.

| Primers | (Orientation) | Sequence |
| --- | --- | --- |
| SI-10 | (R) | 5'-GGAGCATTGCCGTAAAGAT-3' [SEQ ID NO. 26] |
| SI-11 | (F) | 5'-CTATACTCTCCCGGCTAATGATGC-3' [SEQ ID NO. 27] |
| SI-12 | (R) | 5'-CCACCATGCAGGATATTCACTTT-3' [SEQ ID NO. 28] |

Figure 5:
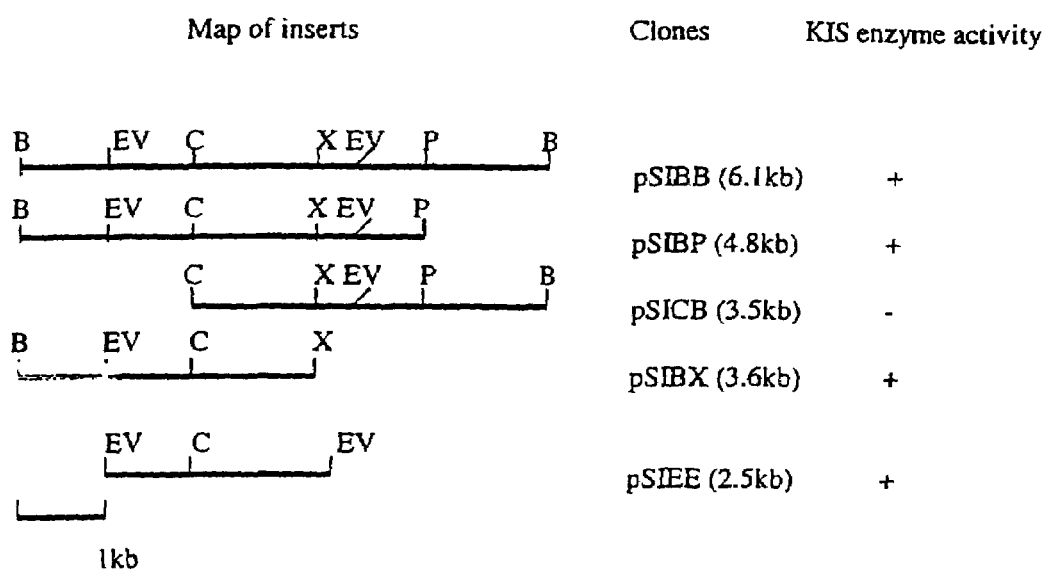
FIG. 5 maps the cloning strategy for the KIS gene from *Klebsiella singaporensis*. The selected clones are incubated for 18 hrs in the LB broth containing 5% sucrose at 37° C. and 200 rpm. The reducing sugar in the broth was determined by the DNS method (Miller, 1959). The insert sizes cloned in the pBluescript II SK(+) are provided in brackets.

The cosmid library of Klebsiella singaporensis was screened for isomaltulose biosynthesis activity. Two positive cosmid clones, designed pPLASI164 and pPLASI169, were selected by their ability to produce reducing sugar, which was confirmed to be isomaltulose by TLC analysis. Restriction enzyme analysis of the two clones revealed that they likely contain the same fragment of ~6.1 kb released by BamHI digestion. Restriction enzyme mapping of the two clones further verified that the clones pPLASI164 and pPLASI169 are identical. The 6.1 kb fragment contains one PstI site, one ClaI site, one XhoI site and two EcoRV sites as shown in FIG. 5. Deletion analysis narrowed down the region encoding isomaltulose biosynthesis to a 2.5 kb EcoRV fragment contained in the clone pSIEE.

The nucleotide sequence of clone pSIEE was determined from both DNA strands FIGS. 6A-6C). Open reading frame (ORF) search revealed the presence of one ORF of 1797 bp nucleotides. Deletion analysis indicates that it is the coding region of isomaltulose synthase gene kis. The putative initiation codon ATG is proceeded at a spacing of 8 bp by a potential ribosome-binding sequence (AAGGA). There is no significant homology to the consensus −35 promoter element (TTGACA). The possible −10 region promoter sequence (TTTAAT), homologous to the consensus promoter sequence (TATAAT) for $\sigma 70$ factor in $E.\ coli$ is observed 44 bp upstream of the initiation codon. A putative sucrose responsive region ($^{-54}$TTTTCTTTAATAACAATT$^{-37}$)[SEQ ID NO.3], an AT-rich sequence, is also located in −10 region which is homologous to the sucrose-responsive region conserved in several sucrose inducible promoters (FIG. 7; Yokoyama et al., 1994). Inducible expression of the kis gene has been confirmed in the presence of sucrose and fructose, whereas there is not kis gene expression when glucose was used as a sole carbon source. The putative core sequence, "CAACTG", the binding motif of helix-loop-helix transcription factors (Murre et al., 1989; Rocha and Gomes, 1998), is located at position 21 bp upstream from the initiation codon site (FIGS. 6A-6C). At the downstream, there are three TCTC boxes, one TCTT box and one TGTG box that closely resemble the TCTG consensus sequence of factor-independent termination sites. Inverted repeated sequences are also found in the downstream of the putative termination codon (TAA). This could create a potential stable hairpin structure, which could block the progression of RNA polymerase (Brendel and Trifonov, 1984).

The cloned kis gene from $K.\ singaporensis$ encodes a protein of 598 amino acids with a calculated molecular weight of 69.94 kDa and an isoelectric point at 6.62 (FIG. 6D). The deduced hydrophilic amino acids are 68.4% of all the amino acids. The best homology to the kis gene is found in the isomaltulose synthase gene from $Enterobacter$ sp. strain SZ62 (Mattes et al., 1998 U.S. Pat. No. 5,786,140), which shares 99.3% identical nucleotides in the open reading frame and 99.7% identical amino acids in the predicted peptide sequences.

The differences are in the C-terminal region of the proteins. KIS has one extra amino acid, Ala577, and two substitutions, with Gly577 and Ala593 in the isomaltulose synthase of strain SZ62 being replaced with Ala578 and Val594, respectively. In addition, the KIS protein shares 67% homology to the same enzyme from the $Protaminobacter\ rubrum$ (Mattes, et al., 1998 U.S. Pat. No. 5,786,140).

A potential sucrose catalytic binding site, "$^{322}$F-D-L-I-R-L-D-R-D-S-N-E$^{332}$" [SEQ ID NO. 4], has been located based on sequence homology comparison with the identified sites of α-glucosyl transferases (FIG. 8). In this motif, two amino acids, arginine and aspartic acid, are highly conserved. The aspartic acid (D) was reported to play a key role in the enzyme activity and its mutation resulted in complete inhibition of the sucrose binding property (Mooser et al., 1991; Kato et al., 1992; Monchois et al., 1997).

REFERENCES

Altschul S F, Madden T L, Schaffer A A, Zhang J H, Zhang Z, Miller W, Lipman D J. 1997. Gapped Blast and PSI-Blast: a new generation of protein database search programs. Nucleic Acids Res. 25:3389-3402.

Bednarek S. and Raikhel N V. 1991. The barley leactin carboxy-terminal propeptide is a vacuolar protein sorting determinant in plants. Plant Cell 3, 1195-1206.

Borisjuk N V, Borisjuk L G, Longendra S, Petersen F, Gleba Y, and Raskin I. 1999. Nature Biotechnology 17, 466-469.

Bower R, and Birch R G. 1992. Transgenic sugarcane plants via microprojectile bombardment. Plant J. 2. 409-416.

Brendel V. and Trifonov E N. 1984. A computer algorithm for testing potential prokaryotic terminators. Nucleic Acids Research 12, 4411-4427.

Bucke, et al. 1982. U.S. Pat. No. 4,359,531.

Bucke, et al. 1987. U.S. Pat. No. 4,670,387.

Cheetham P S J. Imber C E. Isherwood J. 1982. The formation of isomaltulose by immobilized $Erwinia\ rhapontici$. Nature 299, 628-631.

Cheetham P S. 1984. The extraction and mechanism of a novel isomaltulose-synthesizing enzyme from $Erwinia\ rhapontici$. Biochem. J. 220, 213-220.

Devereux J, Hacberli P and Smithies O (1984) A Comprehensive set of sequence analysis program for the VAX Nucleic Acids Res 12, 387-395.

Doetsch, R. N. 1981. Determinative methods of light microscopy, p. 21-33. In D. Gerhard, R. G. E. Murray, R. N. Costilow, E. W. Nester, W. A. Wood, N. R. Krieg, and G. B. Phillips (ed.). Manual of methods for general bacteriology. American Society for Microbiology, Washington, D.C.

Egerer, et al. 1989. U.S. Pat. No. 4,857,461.

Felsenstein J (1989) PHYLIP-phylogeny inference package (version 3.2) Cladistics 5, 164-166

Giffard P M. Simpson C L. Milward C P. and Jacques N A. 1991. Molecular characterization of a cluster of at least two glucosyltransferase genes in $Streptococcus\ salivarius$ ATCC 25975. J. Gen Microbiol 137. 2577-2593.

Hattori T. Fukumoto H. Nakagawa S. Nakaruma K. 1991. Sucrose induced expression of genes coding for the tuberous root storage protein, sporamin of sweet potato in leaves and petioles. Plant Cell Physiol. 32, 79-86.

Helfert C. Gotsche S. and Dahl M K. 1995. Cleavage of trehalose-phosphate in $Bacillus\ subtilis$ is catalyzed by a phosphate-alpha-1,1-glucosidase encoded by the treA gene. Mol. Microbiol. 16, 111-120.

Honda O. Kato C. Kuramitsu H K. 1989. Nucleotide sequence analysis of the *Streptococcus mutans* gtfD gene encoding the glucosyltransferase-S enzyme. J. Gen Microbiol 136, 2099-2105.

Hsu L C, H U M C, Cheng H C, L u J C, and Chung B C. 1993. The N-terminal hydrophobic domain of D450C21 is required for membrane insertion and enzyme stability. J. Biological Chemistry 268, 14682-14686.

Huang J. H., Hsu L. H. and Su Y. C. 1998. Conversion of sucrose to isomaltulose by *Klebsiella* planticola CCRC 19112. J. Industrial Microbiol. Biotechnol. 21, 22-27.

Ishikawa, H., Kudoh, S., Mizutani., T. And Sugitani, T. 1994. Efficacious gum using Isomaltulose (Palatinit). Food industry Tokyo 37, 81-87.

Kato C. Nakano Y. Lis M. Kuramitsu H K. 1992. Molecular genetic analysis of the catalytic site of *Streptococcus mutans* glucosyltransferase. Biochem Biophys Res (189: 1184-1188)

Kawai, K., Yoshikawa, H., Murayama, Y., Okuda, Y. And Yamashita, K. 1989. Usefulness of isomaltulose as a caloric sweetener for diabetic patients. Hormone and Metabolic Research 21, 338-340.

Koes R E. Spelt L E. Mol. J N M. 1989. The chalcone synthase multigene family of *petunia hybrida* (V30): differential light-regulated expression during flower development and UV induction. Plant Mol. Biol. 12. 213-225.

Kunz M. 1993. From sucrose to semisynthetical polymers. In: Carbohydrates as organic Raw Materials II (G. Descotes, ed.) pp 135-161, VCH, Weinheim, N.Y.

Lantero, Jr. 1983. U.S. Pat. No. 4,390,627.

Marmur, J. and Doty P. 1962. Determination of the base composition of deoxyribonucleic acid from its thermal denaturation temperature. J. Mol. Biol. 5: 109-118.

Matsuoka K, and Nakamura K. 1991. Propeptide of a precursor to a plant vacuolar protein required for vacuolar targetting. Proc. Natl. Acad. Sci. USA 88, 834-838.

Mattes R. Klein K. Schiweck H. Kunz M. Munir M. 1998 DNA's encoding isomaltulose synthase and palatinose. U.S. Pat. No. 5,786,140.

McAllister M. Kelly C T. Doyle E and Fogarty W M. 1990. Isomaltulose-synthesizing enzyme of *Serratia plymuthica*. Biotechnol. Lett. 12, 667-672.

Mechold U. Steiner K. Vettermann S and Malke H. 1993. Genetic organization of the streptokinase region of the *Strepcoccus equisimilis* H46A chromosome. Mol. Gen. Gent. 241, 129-140.

Miller G. L. (1959) Use of dinitroaslicylic acid reagent for the determination of reducing sugars. Anal Chem 31, 426-428.

Minami, T., Fujiwara, T., Ooshima, T., Nakajima, Y. and Hamada, S. 1990. Interaction of structural isomers of sucrose in the reaction between sucrose and glucosyl-transferases from mutans streptococci. Oral Microbiology and Immunology 5, 189-194.

Mitsuoka, T. 1990. Bifidobacteria and their role in human health. J. Industri. Microbiol. 6:263-268.

Miyata Y, Sugitani T, Tsuyuki K, Ebashi T and Nakajima Y. 1992 Isolation and characterization of *Pseudomonas mesoacidophila* producing trehalulose Biosci Biotech Biochem 56:1680-1681. Mizutani, T. 1989. Manufacture and application of isomaltulose oligosaccharides. Food Chemicals 5:67-72.

Mollet C, Drancourt M and Raoult D (1997) rpoB sequence analysis as a novel basis for bacterial identification Molecular Microbiology 26, 1005-1011.

Monchois Y. Remaud-Simeon M. Russell R R B. Monsan P F. and Willemot R M. 1997. Characterization of *Leuconostoc mesenteroides* NRRL B-512F dextransucrase (DSRS) and identification of amino-acid residues playing a key role in enzyme activity. Appl Microbiol Biotechnol 48, 465-72.

Monchois Y. Willemot R M. Remaud-Simeon M. Croux C. and Monsan P F. 1996. Cloning and sequencing of a gene coding for a novel dextransucrase from *Leuconostoc mesenteroides* NRRL B-1299 synthesizing only alpha (1,6) and alpha (1,3) linkages. Gene 182, 23-32.

Mooser G. Hefta S A. Paxton R J. Shively J E and Lee T D. 1991. Isolation and sequence of an active site peptide containing a catalytic aspartic acid from two *Streptococcus sobrinus* glucosyltransferase. J. Biol. Chem 266, 8916-8922.

Murre C. McCaw P S. and Baltimore D. 1989. A new DNA binding and dimerization motif in immunogloblin enhancer binding, daughterless, MyD and myoC protein. Cell 56, 777-783.

Nagai Y. Sugitani T. and Tsuyuki K. 1994. Characterization of (α-glucosyltransferase from *Pseudomonas mesoacidophila* MX-45. Biosci Biotech Biochem 58, 1789-1793.

Okamoto S, Tyodayamamoto A, Ito K, Takebe I, Machida Y. 1991. Localization and orientation of the VirD protein of *Agrobacterium tumefaciens* in the cell-membrane. Molecular and General Genetics 228, 24-32.

Palm C J. Costa M A, A n G. Ryan C A. 1990. Wound-inducible nuclear protein binds DNA fragments that regulate a proteinase inhibitor II gene from potato. Proc. Natl. Acad. Sci. USA 87, 603-607

Park Y K. Vegina R T. and Pupin A M. 1992. Conversion of sucrose to isomaltulose by microbial glucosyltransferase. Biotechnol. Lett. 14, 547-551.

Rocha C R C., and Gomes S L. 1998. Isolation, characterization and expression of the gene encoding the beta-subunit of the mitochondrial processing peptidase from *Blastocladiella emersonii*. J. Bacteriol. 180, 3867-3972.

Qrskov I (1984) Genus V *Klebsiella* In Krieg N R (ed.) Bergey's Manual of Systematic Bacteriology vol I pp. 461-465 Williams & Wilkins, Baltimore.

Sambrook J., E. F. Fritsch and T. Maniatis. 1989. Molecular cloning: a laboratory manual, 2nd ed. Cold Spring Harbor Laboratory Press, Cold Spring Harbor, N.Y.

Schiweck H. Munir M. Rapp K M. Schneider R; and Vogel M. 1991. New developments in the use of sucrose as an industrial bulk chemical. In: Carbohydrates as Organic Raw Materials. Ed: Lichtenthaler F W. Pp 57-94. VCH, New York.

Schwimmer, S., and Bevenue, A. 1956. Reagent for differentiation of 1,4- and 1,6-liked glucosaccharides. Science 123, 543-544.

Shiroza T. Ueda S. and Kuramitsu H K 1987. Sequence analysis of the gtfB gene from *Streptococcus mutans*. J. Bacteriol. 169, 4263-4270.

Smibert, R. M., and N. R. Krieg. 1981. General characterization, p. 409-443. In Gerhard, P., R. G. E. Murray, R. N. Costilow, E. W. Nester, W. A. Wood, N. R. Krieg, and G. B. Phillips (ed.). Manual of methods for general bacteriology, American Society for Microbiology, Washington, D.C.

Sporns, P., Plhak, L., and Friedrich, J. 1992. Alberta honey composition. Food Research International 25, 93-100.

Stackebrandt E and Goebel M (19940 Taxonomic note: a place for DND-DNA reassociation and 111 6s rRNA sequence analysis in the present species definition in bacteriology Int J Syst Bacteriol 44, 846-849.

Sugitani, et al. 1993. U.S. Pat. No. 5,229,276.

Sugitani, et al. 1993. U.S. Pat. No. 5,336,617.

Takazoe, I. 1989. Isomaltulose—an isomeric alternative to sucrose. In: Progress in sweeteners, ed. Grenby, T. H. p143-167. Barking, Elsevier Science Publisher.

Topitsoglou V, N Sasaki, I Takazoe and G Frostell 1984 Effect of frequent rinses with isomaltulose (palatinose) solution on acid production in human dental plaque Caries Res 18, 47-51.

Tsuyuki K. Sugitani T. Miyata Y. Ebashi T. and Yakajima Y. 1992. Isolation and characterization of isomaltulose and trehalulose-producing bacteria from Thailand soil. J. Gen. Appl. Microbiol. 38, 483-490.

Twell D. and Ooms G. 1988. Structural diversity of the patatin gene family in potato Desiree. Mol. Gen Genet 212, 325-336.

Ueda S. Shiroza T. and Kuramitsu H K. 1987-1988. Sequence analysis of the gtfc gene from *Streptococcus mutans* GS5. Gene 69, 101-109.

Van den Broeck G, Timko M P, Kausch A P, Cashmore A R, Van Montagu M, Herrera-Estrella L. 1995. Targetting of a foreign protein to chloroplasts by fusion to the transit peptide from the small subunit of ribulose 1,5-bisphosphate carboxylase. Nature 313, 358-363.

Wilke-Douglas M, Perchorowicz J T, Houck C M, and Thomas B R. 1989. Methods and compositions for altering physical characteristics of fruit and fruit products. PCT Patent WO 89 12386.

Yamamoto M. and Horikoshi K. 1990. Hydrolysis of 1,6-alpha-D-glucosidic linkages in isomaltose and dextrins produced from starch and glycogen by alpha-amylase. Denpun Kagaku 37, 137-144.

Yokoyama R. Hirose T. Fujii N. Aspuria E J, Kato A., Uchimiya H. 1994. The rolC promoter of *Agrobacterium rhizogenes* Ri plasmid is activated by sucrose in transgenic tobacco plants. Mol Gen Genet 244, 15-22.

Zhang L, Xu J, and Birch R G. 1999. Engineered detoxification confers resistance against a pathogenic bacterium. Nature Biotechnology 17, 1021-1024.

We claim:

1. An isolated nucleic acid sequence encoding a *Klebsiella* isomaltulose synthase (KIS), wherein said KIS comprises the amino acid sequence as set forth in SEQ ID NO:2.

2. The nucleic acid sequence of claim 1 comprising the nucleotide sequence as set forth in SEQ ID NO:1.

3. The nucleic acid sequence of claim 1 which comprises nucleotides 214 through 2007 of the nucleotide sequence as set forth in SEQ ID NO:1.

4. An expression vector which comprises the nucleic acid of claim 1, wherein the expression vector is capable of propagating in a procaryotic or eucaryotic cell.

5. A cell of a procaryote or eukaryote transformed or transfected with the expression vector of claim 4.

6. A method for producing isomaltulose in a plant, comprising the steps of introducing into a cell of such plant a nucleic acid comprising a nucleic acid sequence which encodes a *Klebsiella isomaltulose* synthase (KIS), said KIS comprising the amino acid sequence as set forth in SEQ ID NO:2, in a manner which allows said cell to express said nucleic acid and
Expressing said nucleic acid in said cell;
Thereby producing the isomaltulose in a plant comprising said cell.

7. The method of claim 6, wherein the nucleic acid sequence comprises the nucleotide sequence as set forth in SEQ ID NO:1.

8. The method of claim 6, wherein the nucleic acid sequence comprises nucleotides 214 through 2007 of the nucleotide sequence as set forth in SEQ ID NO:1.

9. The method of claim 6, wherein the nucleic acid further comprises a membrane attachment domain coding sequence operably linked to the KIS-encoding nucleic acid sequence.

10. The method of claim 6, wherein said KIS-encoding nucleic acid sequence is fused to the 3' end of a nucleic acid sequence encoding a signal peptide.

11. The method of claim 10, wherein the signal peptide is a vacuole targeting signal peptide.

12. The method of claim 8, wherein the KIS-encoding nucleic acid sequence is fused toe the 3' end of a nucleic acid sequence encoding a signal peptide.

13. The method of claim 6, wherein the plant is selected from the group consisting of sugarcane, maize, watermelon, and sugarbeet.

14. A nucleic acid comprising the nucleic acid sequence of claim 3 fused to the 3' end of a nucleic acid sequence encoding a signal peptide.

15. The method of claim 12, wherein the signal peptide is a vacuole targeting signal peptide.

* * * * *

SEQUENCE LISTING

```
<160> NUMBER OF SEQ ID NOS: 42

<210> SEQ ID NO 1
<211> LENGTH: 2477
<212> TYPE: DNA
<213> ORGANISM: Klebsiella singaporensis
<220> FEATURE:
<221> NAME/KEY: CDS
<222> LOCATION: (214)..(2007)
<220> FEATURE:
<221> NAME/KEY: misc_feature
<222> LOCATION: (1908)..(1920)
<223> OTHER INFORMATION: n may be any nucleotide

<400> SEQUENCE: 1
gatatcactg gtattatgga gtattatact cccccttat ttactcatca aagccaggcg      60
ttccactctg cctccggtat ataactttcc gggaaacaat cccttcctga aaataattat    120
tgttaccgga gtcatactct ggctattgat gatttacgct tttctttaat aacaattcgt    180
ctcattcaca actgactttg caaggaaatt att atg tct ttt gtt acg cta cgt    234
                                    Met Ser Phe Val Thr Leu Arg
                                    1               5 acc ggg gtg gct gtc gcg ctg tca tct ttg ata ata agt ctg gcc tgc      282
Thr Gly Val Ala Val Ala Leu Ser Ser Leu Ile Ile Ser Leu Ala Cys
        10                  15                  20 ccg gct gtc agt gct gca cca tcc ttg aat cag gat att cac gtt caa     330
Pro Ala Val Ser Ala Ala Pro Ser Leu Asn Gln Asp Ile His Val Gln
    25                  30                  35 aag gaa agt gaa tat cct gca tgg tgg aaa gaa gct gtt ttt tat cag     378
Lys Glu Ser Glu Tyr Pro Ala Trp Trp Lys Glu Ala Val Phe Tyr Gln
40                  45                  50                  55 atc tat cct cgc tca ttt aaa gac acc aat gat gat ggc att ggc gat     426
Ile Tyr Pro Arg Ser Phe Lys Asp Thr Asn Asp Asp Gly Ile Gly Asp
                60                  65                  70 att cgc ggt att att gaa aag ctg gac tat ctg aaa tcg ctc ggt att     474
Ile Arg Gly Ile Ile Glu Lys Leu Asp Tyr Leu Lys Ser Leu Gly Ile
            75                  80                  85
```

```
gac gct atc tgg atc aat ccc cat tac gac tct ccg aac acc gat aac      522
Asp Ala Ile Trp Ile Asn Pro His Tyr Asp Ser Pro Asn Thr Asp Asn
    90              95                  100 ggc tat gac atc agt aat tat cgt cag ata atg aaa gag tat ggc aca      570
Gly Tyr Asp Ile Ser Asn Tyr Arg Gln Ile Met Lys Glu Tyr Gly Thr
        105                 110                 115 atg gag gat ttt gat agc ctt gtt gcc gaa atg aaa aaa cga aat atg      618
Met Glu Asp Phe Asp Ser Leu Val Ala Glu Met Lys Lys Arg Asn Met
120             125                 130                 135 cgc tta atg atc gac gtg gtc att aac cat acc agt gat caa cac ccg      666
Arg Leu Met Ile Asp Val Val Ile Asn His Thr Ser Asp Gln His Pro
                140                 145                 150 tgg ttt att cag agt aaa agc gat aaa aac aac cct tat cgt gac tat      714
Trp Phe Ile Gln Ser Lys Ser Asp Lys Asn Asn Pro Tyr Arg Asp Tyr
                155                 160                 165 tat ttc tgg cgt gac gga aaa gat aat cag cca cct aat aat tac ccc      762
Tyr Phe Trp Arg Asp Gly Lys Asp Asn Gln Pro Pro Asn Asn Tyr Pro
            170                 175                 180 tca ttt ttc ggc ggc tcg gca tgg caa aaa gat gca aag tca gga cag      810
Ser Phe Phe Gly Gly Ser Ala Trp Gln Lys Asp Ala Lys Ser Gly Gln
185                 190                 195 tac tat tta cac tat ttt gcc aga cag caa cct gat ctc aac tgg gat      858
Tyr Tyr Leu His Tyr Phe Ala Arg Gln Gln Pro Asp Leu Asn Trp Asp
200                 205                 210                 215 aac ccg aaa gta cgt gag gat ctt tac gca atg ctc cgc ttc tgg ctg      906
Asn Pro Lys Val Arg Glu Asp Leu Tyr Ala Met Leu Arg Phe Trp Leu
                220                 225                 230 gat aaa ggc gtt tca ggc atg cga ttt gat acg gtg gca act tat tcc      954
Asp Lys Gly Val Ser Gly Met Arg Phe Asp Thr Val Ala Thr Tyr Ser
                235                 240                 245 aaa atc ccg gga ttt ccc aat ctg aca cct gaa caa cag aaa aat ttt     1002
Lys Ile Pro Gly Phe Pro Asn Leu Thr Pro Glu Gln Gln Lys Asn Phe
            250                 255                 260 gct gaa caa tac acc atg ggg cct aat att cat cga tac att cag gaa     1050
Ala Glu Gln Tyr Thr Met Gly Pro Asn Ile His Arg Tyr Ile Gln Glu
265                 270                 275 atg aac cgg aaa gtt ctg tcc cgg tat gat gtg gcc acc gcg ggt gaa     1098
Met Asn Arg Lys Val Leu Ser Arg Tyr Asp Val Ala Thr Ala Gly Glu
280                 285                 290                 295 att ttt ggc gtc ccg ctg gat cgt tcg tcg cag ttt ttt gat cgc cgc     1146
Ile Phe Gly Val Pro Leu Asp Arg Ser Ser Gln Phe Phe Asp Arg Arg
                300                 305                 310 cga cat gag ctg aat atg gcg ttt atg ttt gac ctc att cgt ctc gat     1194
Arg His Glu Leu Asn Met Ala Phe Met Phe Asp Leu Ile Arg Leu Asp
            315                 320                 325 cgc gac agc aat gaa cgc tgg cgt cac aag tcg tgg tcg ctc tct cag     1242
Arg Asp Ser Asn Glu Arg Trp Arg His Lys Ser Trp Ser Leu Ser Gln
            330                 335                 340 ttc cgc cag atc atc agc aaa atg gat gtc acg gtc gga aag tat ggc     1290
Phe Arg Gln Ile Ile Ser Lys Met Asp Val Thr Val Gly Lys Tyr Gly
            345                 350                 355 tgg aac acg ttc ttc tta gat aac cat gac aac ccc cgt gcg gta tct     1338
Trp Asn Thr Phe Phe Leu Asp Asn His Asp Asn Pro Arg Ala Val Ser
360                 365                 370                 375 cac ttc ggg gat gac agg ccg caa tgg cgg gag gcg tcg gct aag gca     1386
His Phe Gly Asp Asp Arg Pro Gln Trp Arg Glu Ala Ser Ala Lys Ala
                380                 385                 390 ctg gcg acg att acc ctc act cag cgg gcg acg ccg ttt att tat cag     1434
Leu Ala Thr Ile Thr Leu Thr Gln Arg Ala Thr Pro Phe Ile Tyr Gln
            395                 400                 405
```

```
ggt tca gag ctg gga atg act aat tat ccc ttc agg caa ctc aac gaa    1482
Gly Ser Glu Leu Gly Met Thr Asn Tyr Pro Phe Arg Gln Leu Asn Glu
        410                 415                 420 ttt gac gac atc gag gtc aaa ggt ttc tgg cag gat tat gtc cag agt    1530
Phe Asp Asp Ile Glu Val Lys Gly Phe Trp Gln Asp Tyr Val Gln Ser
    425                 430                 435 gga aaa gtc acg gcc aca gag ttt ctc gat aat gtg cgc ctg acg agc    1578
Gly Lys Val Thr Ala Thr Glu Phe Leu Asp Asn Val Arg Leu Thr Ser
440                 445                 450                 455 cgc gat aac agc aga aca cct ttc cag tgg aat gac acc ctg aat gct    1626
Arg Asp Asn Ser Arg Thr Pro Phe Gln Trp Asn Asp Thr Leu Asn Ala
            460                 465                 470 ggt ttt act cgc gga aag ccg tgg ttt cac atc aac cca aac tat gtg    1674
Gly Phe Thr Arg Gly Lys Pro Trp Phe His Ile Asn Pro Asn Tyr Val
                475                 480                 485 gag atc aac gcc gaa cgc gaa gaa acc cgc gaa gat tca gtg ctg aat    1722
Glu Ile Asn Ala Glu Arg Glu Glu Thr Arg Glu Asp Ser Val Leu Asn
        490                 495                 500 tac tat aaa aaa atg att cag cta cgc cac cat atc cct gct ctg gta    1770
Tyr Tyr Lys Lys Met Ile Gln Leu Arg His His Ile Pro Ala Leu Val
    505                 510                 515 tat ggc gcc tat cag gat ctt aat cca cag gac aat acc gtt tat gcc    1818
Tyr Gly Ala Tyr Gln Asp Leu Asn Pro Gln Asp Asn Thr Val Tyr Ala
520                 525                 530                 535 tat acc cga acg ctg ggt aac gag cgt tat ctg gtc gtg gtg aac ttt    1866
Tyr Thr Arg Thr Leu Gly Asn Glu Arg Tyr Leu Val Val Val Asn Phe
            540                 545                 550 aag gag tac ccg gtc cgc tat act ctc ccg gct aat gat gcn ath gar    1914
Lys Glu Tyr Pro Val Arg Tyr Thr Leu Pro Ala Asn Asp Ala Ile Glu
                555                 560                 565 gar gtn gtc att gat act cag cag cag gcg gct gcg ccg cac agc aca    1962
Glu Val Val Ile Asp Thr Gln Gln Gln Ala Ala Ala Pro His Ser Thr
        570                 575                 580 tcc ctg tca ttg agc ccc tgg cag gca ggt gtg tat aag ctg cgg        2007
Ser Leu Ser Leu Ser Pro Trp Gln Ala Gly Val Tyr Lys Leu Arg
    585                 590                 595 taatcacctg ggggattgat gacaagttcc ccagacaata gagttttcca ggtctttagc    2067
actgctgtgc tcagcgatag ttgtgctctc ctgtgacttc gtaagtgcct gtctcatggc    2127
aggcattgtc aggtcagaag ccttctcagg cagcctcgag taacagcgcc cagttagcat    2187 cccccctgaaa gatgggggt atgtataaat tagcgttaaa gaacatgaac cagccaccgt    2247
catcttatca accaacaggc gagatgagct ccgattcctg attcttcaca ttgccgttga    2307
tgcgcctgaa gcctcgccct ttagggccgg gaaataagca cagcatctgg cgatctcttt    2367
tgccacttta ctgatcacat ccggcctcat ccatttccgg gcggcttcag ccatcaggag    2427
aaagggtagt ggtcgtgtat atgagccagg ccaaaaaaag gtgtgatatc               2477

<210> SEQ ID NO 2
<211> LENGTH: 598
<212> TYPE: PRT
<213> ORGANISM: Klebsiella singaporensis

<400> SEQUENCE: 2

Met Ser Phe Val Thr Leu Arg Thr Gly Val Ala Val Ala Leu Ser Ser
 1               5                  10                  15

Leu Ile Ile Ser Leu Ala Cys Pro Ala Val Ser Ala Ala Pro Ser Leu
            20                  25                  30
```

```
Asn Gln Asp Ile His Val Gln Lys Glu Ser Glu Tyr Pro Ala Trp Trp
         35                  40                  45
Lys Glu Ala Val Phe Tyr Gln Ile Tyr Pro Arg Ser Phe Lys Asp Thr
 50                  55                  60
Asn Asp Asp Gly Ile Gly Asp Ile Arg Gly Ile Ile Glu Lys Leu Asp
 65                  70                  75                  80
Tyr Leu Lys Ser Leu Gly Ile Asp Ala Ile Trp Ile Asn Pro His Tyr
                 85                  90                  95
Asp Ser Pro Asn Thr Asp Asn Gly Tyr Asp Ile Ser Asn Tyr Arg Gln
             100                 105                 110
Ile Met Lys Glu Tyr Gly Thr Met Glu Asp Phe Asp Ser Leu Val Ala
         115                 120                 125
Glu Met Lys Lys Arg Asn Met Arg Leu Met Ile Asp Val Val Ile Asn
 130                 135                 140
His Thr Ser Asp Gln His Pro Trp Phe Ile Gln Ser Lys Ser Asp Lys
145                 150                 155                 160
Asn Asn Pro Tyr Arg Asp Tyr Tyr Phe Trp Arg Asp Gly Lys Asp Asn
                 165                 170                 175
Gln Pro Pro Asn Asn Tyr Pro Ser Phe Phe Gly Gly Ser Ala Trp Gln
             180                 185                 190
Lys Asp Ala Lys Ser Gly Gln Tyr Tyr Leu His Tyr Phe Ala Arg Gln
         195                 200                 205
Gln Pro Asp Leu Asn Trp Asp Asn Pro Lys Val Arg Glu Asp Leu Tyr
 210                 215                 220
Ala Met Leu Arg Phe Trp Leu Asp Lys Gly Val Ser Gly Met Arg Phe
225                 230                 235                 240
Asp Thr Val Ala Thr Tyr Ser Lys Ile Pro Gly Phe Pro Asn Leu Thr
                 245                 250                 255
Pro Glu Gln Gln Lys Asn Phe Ala Glu Gln Tyr Thr Met Gly Pro Asn
             260                 265                 270
Ile His Arg Tyr Ile Gln Glu Met Asn Arg Lys Val Leu Ser Arg Tyr
         275                 280                 285
Asp Val Ala Thr Ala Gly Glu Ile Phe Gly Val Pro Leu Asp Arg Ser
 290                 295                 300
Ser Gln Phe Phe Asp Arg Arg His Glu Leu Asn Met Ala Phe Met
305                 310                 315                 320
Phe Asp Leu Ile Arg Leu Asp Arg Asp Ser Asn Glu Arg Trp Arg His
                 325                 330                 335
Lys Ser Trp Ser Leu Ser Gln Phe Arg Gln Ile Ile Ser Lys Met Asp
             340                 345                 350
Val Thr Val Gly Lys Tyr Gly Trp Asn Thr Phe Phe Leu Asp Asn His
         355                 360                 365
Asp Asn Pro Arg Ala Val Ser His Phe Gly Asp Asp Arg Pro Gln Trp
 370                 375                 380
Arg Glu Ala Ser Ala Lys Ala Leu Ala Thr Ile Thr Leu Thr Gln Arg
385                 390                 395                 400
Ala Thr Pro Phe Ile Tyr Gln Gly Ser Glu Leu Gly Met Thr Asn Tyr
                 405                 410                 415
Pro Phe Arg Gln Leu Asn Glu Phe Asp Asp Ile Glu Val Lys Gly Phe
             420                 425                 430
Trp Gln Asp Tyr Val Gln Ser Gly Lys Val Thr Ala Thr Glu Phe Leu
         435                 440                 445
Asp Asn Val Arg Leu Thr Ser Arg Asp Asn Ser Arg Thr Pro Phe Gln
```

-continued

```
            450                 455                 460
Trp Asn Asp Thr Leu Asn Ala Gly Phe Thr Arg Gly Lys Pro Trp Phe
465                 470                 475                 480

His Ile Asn Pro Asn Tyr Val Glu Ile Asn Ala Glu Arg Glu Thr
                485                 490                 495

Arg Glu Asp Ser Val Leu Asn Tyr Tyr Lys Lys Met Ile Gln Leu Arg
            500                 505                 510

His His Ile Pro Ala Leu Val Tyr Gly Ala Tyr Gln Asp Leu Asn Pro
            515                 520                 525

Gln Asp Asn Thr Val Tyr Ala Tyr Thr Arg Thr Leu Gly Asn Glu Arg
            530                 535                 540

Tyr Leu Val Val Asn Phe Lys Glu Tyr Pro Val Arg Tyr Thr Leu
545                 550                 555                 560

Pro Ala Asn Asp Ala Ile Glu Glu Val Val Ile Asp Thr Gln Gln Gln
                565                 570                 575

Ala Ala Ala Pro His Ser Thr Ser Leu Ser Leu Ser Pro Trp Gln Ala
            580                 585                 590

Gly Val Tyr Lys Leu Arg
            595
```

<210> SEQ ID NO 3
<211> LENGTH: 18
<212> TYPE: DNA
<213> ORGANISM: Klebsiella singaporensis

<400> SEQUENCE: 3
ttttctttaa taacaatt                                                 18

<210> SEQ ID NO 4
<211> LENGTH: 12
<212> TYPE: PRT
<213> ORGANISM: Klebsiella singaporensis

<400> SEQUENCE: 4

Phe Asp Leu Ile Arg Leu Asp Arg Asp Ser Asn Glu
 1               5                  10

<210> SEQ ID NO 5
<211> LENGTH: 20
<212> TYPE: DNA
<213> ORGANISM: Artificial Sequence
<220> FEATURE:
<223> OTHER INFORMATION: Description of Artificial Sequence: primer
      sequences used for sequencing of the kis gene

<400> SEQUENCE: 5
tgacgagtgg cggacgggtg                                               20

<210> SEQ ID NO 6
<211> LENGTH: 22
<212> TYPE: DNA
<213> ORGANISM: Artificial Sequence
<220> FEATURE:
<223> OTHER INFORMATION: Description of Artificial Sequence: primer
      sequences used for sequencing of the kis gene

<400> SEQUENCE: 6
ccatggtgtg acgggcggtg tg                                            22

<210> SEQ ID NO 7
<211> LENGTH: 20

```
<212> TYPE: DNA
<213> ORGANISM: Artificial Sequence
<220> FEATURE:
<223> OTHER INFORMATION: Description of Artificial Sequence: primer
      sequences used for sequencing of the kis gene

<400> SEQUENCE: 7
tgacgagtgg cggacgggtg                                              20

<210> SEQ ID NO 8
<211> LENGTH: 22
<212> TYPE: DNA
<213> ORGANISM: Artificial Sequence
<220> FEATURE:
<223> OTHER INFORMATION: Description of Artificial Sequence: primer
      sequences used for sequencing of the kis gene

<400> SEQUENCE: 8
ccatggtgtg acgggcggtg tg                                           22

<210> SEQ ID NO 9
<211> LENGTH: 24
<212> TYPE: DNA
<213> ORGANISM: Artificial Sequence
<220> FEATURE:
<223> OTHER INFORMATION: Description of Artificial Sequence: primer
      sequences used for sequencing of the kis gene

<400> SEQUENCE: 9
tacgggaggc agcagtgggg aata                                         24

<210> SEQ ID NO 10
<211> LENGTH: 20
<212> TYPE: DNA
<213> ORGANISM: Artificial Sequence
<220> FEATURE:
<223> OTHER INFORMATION: Description of Artificial Sequence: primer
      sequences used for sequencing of the kis gene

<400> SEQUENCE: 10
atgcagttcc caggttgagc                                              20

<210> SEQ ID NO 11
<211> LENGTH: 21
<212> TYPE: DNA
<213> ORGANISM: Artificial Sequence
<220> FEATURE:
<223> OTHER INFORMATION: Description of Artificial Sequence: primer
      sequences used for sequencing of the kis gene

<400> SEQUENCE: 11
gaaatccccg ggctcaacct g                                            21

<210> SEQ ID NO 12
<211> LENGTH: 24
<212> TYPE: DNA
<213> ORGANISM: Artificial Sequence
<220> FEATURE:
<223> OTHER INFORMATION: Description of Artificial Sequence: primer
      sequences used for sequencing of the kis gene

<400> SEQUENCE: 12
acatcgttta cggcgtggac tacc                                         24

<210> SEQ ID NO 13
<211> LENGTH: 24
<212> TYPE: DNA
```

```
<213> ORGANISM: Artificial Sequence
<220> FEATURE:
<223> OTHER INFORMATION: Description of Artificial Sequence: primer
      sequences used for sequencing of the kis gene

<400> SEQUENCE: 13
ggccgcaagg ttaaaactca aatg                                          24

<210> SEQ ID NO 14
<211> LENGTH: 20
<212> TYPE: DNA
<213> ORGANISM: Artificial Sequence
<220> FEATURE:
<223> OTHER INFORMATION: Description of Artificial Sequence: primer
      sequences used for sequencing of the kis gene

<400> SEQUENCE: 14
ccggaccgct ggcaacaaag                                               20

<210> SEQ ID NO 15
<211> LENGTH: 18
<212> TYPE: DNA
<213> ORGANISM: Artificial Sequence
<220> FEATURE:
<223> OTHER INFORMATION: Description of Artificial Sequence: primer
      sequences used for sequencing of the kis gene

<400> SEQUENCE: 15
cagttccgcg ttggcctg                                                 18

<210> SEQ ID NO 16
<211> LENGTH: 20
<212> TYPE: DNA
<213> ORGANISM: Artificial Sequence
<220> FEATURE:
<223> OTHER INFORMATION: Description of Artificial Sequence: primer
      sequences used for sequencing of the kis gene

<400> SEQUENCE: 16
cggttggcgt catcgtgttc                                               20

<210> SEQ ID NO 17
<211> LENGTH: 22
<212> TYPE: DNA
<213> ORGANISM: Artificial Sequence
<220> FEATURE:
<223> OTHER INFORMATION: Description of Artificial Sequence: primer
      sequences used for sequencing of the kis gene

<400> SEQUENCE: 17
cccgctggca atatttctga ct                                            22

<210> SEQ ID NO 18
<211> LENGTH: 24
<212> TYPE: DNA
<213> ORGANISM: Artificial Sequence
<220> FEATURE:
<223> OTHER INFORMATION: Description of Artificial Sequence: primer
      sequences used for sequencing of the kis gene

<400> SEQUENCE: 18
cacgaccact accctttctc ctga                                          24

<210> SEQ ID NO 19
<211> LENGTH: 24
<212> TYPE: DNA
<213> ORGANISM: Artificial Sequence
```

```
<220> FEATURE:
<223> OTHER INFORMATION: Description of Artificial Sequence: primer
      sequences used for sequencing of the kis gene

<400> SEQUENCE: 19
cctcgcctca tttaaagaca ccaa                                          24

<210> SEQ ID NO 20
<211> LENGTH: 22
<212> TYPE: DNA
<213> ORGANISM: Artificial Sequence
<220> FEATURE:
<223> OTHER INFORMATION: Description of Artificial Sequence: primer
      sequences used for sequencing of the kis gene

<400> SEQUENCE: 20
taggcgccat ataccagagc ag                                            22

<210> SEQ ID NO 21
<211> LENGTH: 24
<212> TYPE: DNA
<213> ORGANISM: Artificial Sequence
<220> FEATURE:
<223> OTHER INFORMATION: Description of Artificial Sequence: primer
      sequences used for sequencing of the kis gene

<400> SEQUENCE: 21
cgtgactatt atttctggcg tgac                                          24

<210> SEQ ID NO 22
<211> LENGTH: 22
<212> TYPE: DNA
<213> ORGANISM: Artificial Sequence
<220> FEATURE:
<223> OTHER INFORMATION: Description of Artificial Sequence: primer
      sequences used for sequencing of the kis gene

<400> SEQUENCE: 22
cgtcgcccgc tgagtgaggt aa                                            22

<210> SEQ ID NO 23
<211> LENGTH: 18
<212> TYPE: DNA
<213> ORGANISM: Artificial Sequence
<220> FEATURE:
<223> OTHER INFORMATION: Description of Artificial Sequence: primer
      sequences used for sequencing of the kis gene

<400> SEQUENCE: 23
tagataacca tgacaacc                                                 18

<210> SEQ ID NO 24
<211> LENGTH: 19
<212> TYPE: DNA
<213> ORGANISM: Artificial Sequence
<220> FEATURE:
<223> OTHER INFORMATION: Description of Artificial Sequence: primer
      sequences used for sequencing of the kis gene

<400> SEQUENCE: 24
gcggtggcca catcatacc                                                19

<210> SEQ ID NO 25
<211> LENGTH: 24
<212> TYPE: DNA
<213> ORGANISM: Artificial Sequence
<220> FEATURE:
```

```
<223> OTHER INFORMATION: Description of Artificial Sequence: primer
      sequences used for sequencing of the kis gene

<400> SEQUENCE: 25
cgccgtttat ttatcaaggt tcag                                        24

<210> SEQ ID NO 26
<211> LENGTH: 19
<212> TYPE: DNA
<213> ORGANISM: Artificial Sequence
<220> FEATURE:
<223> OTHER INFORMATION: Description of Artificial Sequence: primer
      sequences used for sequencing of the kis gene

<400> SEQUENCE: 26
ggagcattgc cgtaaagat                                              19

<210> SEQ ID NO 27
<211> LENGTH: 24
<212> TYPE: DNA
<213> ORGANISM: Artificial Sequence
<220> FEATURE:
<223> OTHER INFORMATION: Description of Artificial Sequence: primer
      sequences used for sequencing of the kis gene

<400> SEQUENCE: 27
ctatactctc ccggctaatg atgc                                        24

<210> SEQ ID NO 28
<211> LENGTH: 23
<212> TYPE: DNA
<213> ORGANISM: Artificial Sequence
<220> FEATURE:
<223> OTHER INFORMATION: Description of Artificial Sequence: primer
      sequences used for sequencing of the kis gene

<400> SEQUENCE: 28
ccaccatgca ggatattcac ttt                                         23

<210> SEQ ID NO 29
<211> LENGTH: 18
<212> TYPE: DNA
<213> ORGANISM: Agrobacterium rhizogenes

<400> SEQUENCE: 29
attaattaat aaatttgt                                               18

<210> SEQ ID NO 30
<211> LENGTH: 18
<212> TYPE: DNA
<213> ORGANISM: Potato

<400> SEQUENCE: 30
attaattatt atttttcc                                               18

<210> SEQ ID NO 31
<211> LENGTH: 18
<212> TYPE: DNA
<213> ORGANISM: Potato

<400> SEQUENCE: 31
attatataat actaataa                                               18

<210> SEQ ID NO 32
<211> LENGTH: 18
```

<212> TYPE: DNA
<213> ORGANISM: Petunia sp.

<400> SEQUENCE: 32
attatgtcat aaattcta                                              18

<210> SEQ ID NO 33
<211> LENGTH: 18
<212> TYPE: DNA
<213> ORGANISM: Sweet potato

<400> SEQUENCE: 33
cttaatttac taatttgg                                              18

<210> SEQ ID NO 34
<211> LENGTH: 12
<212> TYPE: PRT
<213> ORGANISM: Bacillus coagulans

<400> SEQUENCE: 34

Val Asp Gly Trp Arg Met Asp Val Ile Gly Ser Ile
 1               5                  10

<210> SEQ ID NO 35
<211> LENGTH: 12
<212> TYPE: PRT
<213> ORGANISM: Bacillus subtilis

<400> SEQUENCE: 35

Ile Asp Gly Phe Arg Leu Asp Val Ile Asn Leu Ile
 1               5                  10

<210> SEQ ID NO 36
<211> LENGTH: 12
<212> TYPE: PRT
<213> ORGANISM: Streptococcus equisimilis

<400> SEQUENCE: 36

Ile Gly Gly Phe Arg Met Asp Val Ile Asp Leu Ile
 1               5                  10

<210> SEQ ID NO 37
<211> LENGTH: 12
<212> TYPE: PRT
<213> ORGANISM: L. mesenteroides NRRL B-512F

<400> SEQUENCE: 37

Phe Asp Gly Ile Arg Val Asp Ala Val Asp Asn Val
 1               5                  10

<210> SEQ ID NO 38
<211> LENGTH: 12
<212> TYPE: PRT
<213> ORGANISM: L. mesenteroides NRRL B-1299

<400> SEQUENCE: 38

Phe Asp Gly Tyr Arg Val Asp Ala Val Asp Asn Val
 1               5                  10

<210> SEQ ID NO 39
<211> LENGTH: 12
<212> TYPE: PRT
<213> ORGANISM: S. mutans GS5

<400> SEQUENCE: 39

```
Phe Asp Ser Ile Arg Val Asp Ala Val Asp Asn Val
 1               5                  10

<210> SEQ ID NO 40
<211> LENGTH: 12
<212> TYPE: PRT
<213> ORGANISM: S. mutans GS5

<400> SEQUENCE: 40

Phe Asp Gly Val Arg Val Asp Ala Val Asp Asn Val
 1               5                  10

<210> SEQ ID NO 41
<211> LENGTH: 12
<212> TYPE: PRT
<213> ORGANISM: Bacillus sp.

<400> SEQUENCE: 41

Val Asp Gly Trp Arg Met Asp Val Ile Gly Ser Ile
 1               5                  10

<210> SEQ ID NO 42
<211> LENGTH: 12
<212> TYPE: PRT
<213> ORGANISM: S. salivarius ATCC25975

<400> SEQUENCE: 42

Phe Asp Gly Ile Arg Val Asp Ala Val Asp Asn Val
 1               5                  10
```